(12) United States Patent
Kurfirst

(10) Patent No.: US 11,232,698 B1
(45) Date of Patent: Jan. 25, 2022

(54) SYSTEMS AND METHODS FOR USING SMART PILL BOTTLES TO DISPLAY PRESCRIPTION INFORMATION TO USERS

(71) Applicant: Aetna Inc., Hartford, CT (US)

(72) Inventor: Dwayne Kurfirst, Hartford, CT (US)

(73) Assignee: Aetna Inc., Hartford, CT (US)

( * ) Notice: Subject to any disclaimer, the term of this patent is extended or adjusted under 35 U.S.C. 154(b) by 15 days.

(21) Appl. No.: 16/931,370

(22) Filed: Jul. 16, 2020

(51) Int. Cl.
| | |
|---|---|
| G08B 21/00 | (2006.01) |
| G08B 21/24 | (2006.01) |
| G08B 5/22 | (2006.01) |
| G16H 20/13 | (2018.01) |
| G07F 9/02 | (2006.01) |
| A61J 7/02 | (2006.01) |
| A61J 7/00 | (2006.01) |
| A61J 1/03 | (2006.01) |
| G06F 3/14 | (2006.01) |

(52) U.S. Cl.
CPC ............. *G08B 21/24* (2013.01); *A61J 1/03* (2013.01); *A61J 7/0076* (2013.01); *A61J 7/02* (2013.01); *G07F 9/023* (2013.01); *G08B 5/22* (2013.01); *G16H 20/13* (2018.01); *A61J 2200/70* (2013.01); *A61J 2205/50* (2013.01); *G06F 3/14* (2013.01)

(58) Field of Classification Search
CPC .... G08B 21/24; G08B 5/22; A61J 1/03; A61J 7/0076; A61J 7/02; A61J 2205/50; A61J 2200/70; G16H 20/13; G07F 9/023; G06F 3/14
USPC ...................................................... 340/691.6
See application file for complete search history.

(56) References Cited

U.S. PATENT DOCUMENTS

| | | | | |
|---|---|---|---|---|
| 5,020,037 | A * | 5/1991 | Raven | A61J 7/0481 221/2 |
| 8,708,192 | B2 * | 4/2014 | Flowers | A61J 7/0409 221/5 |
| 8,727,180 | B2 | 5/2014 | Zonana et al. | |
| 2006/0071011 | A1 * | 4/2006 | Varvarelis | G07F 17/0092 221/9 |
| 2010/0270257 | A1 | 10/2010 | Wachman et al. | |
| 2015/0341302 | A1 * | 11/2015 | Balachandran | G08B 5/36 340/815.4 |

(Continued)

OTHER PUBLICATIONS

AdhereTech https://www.adheretech.com/ (2019).

(Continued)

*Primary Examiner* — Mark S Rushing
(74) *Attorney, Agent, or Firm* — Leydig, Voit & Mayer, Ltd.

(57) ABSTRACT

In some instances, a method performed by a smart pill bottle delivery device is provided. The method comprises determining one or more prescription timing intervals indicating times for the user to take one or more medication units of the medication based on retrieving a prescription for the user from memory, providing one or more visual notifications indicating for the user to take the one or more medication units based on the one or more prescription timing intervals, subsequent to providing the one or more visual notifications, detecting position information indicating an action performed by the user, and causing display of a second display screen based on the position information indicating the action performed by the user.

20 Claims, 14 Drawing Sheets

(56) References Cited

U.S. PATENT DOCUMENTS

| | | | |
|---|---|---|---|
| 2016/0026773 A1* | 1/2016 | Chu | G01L 5/00 |
| | | | 705/2 |
| 2016/0324726 A1 | 11/2016 | Roberts et al. | |
| 2019/0392934 A1* | 12/2019 | Tabakin | G16H 10/60 |

OTHER PUBLICATIONS

"CMT Medication Management Platform," https://cmtcares.com/solutions/ (© 2017-2019).

Comstock, Jonah, "GlowCaps now sold through CVS, new randomized control trial launches," https://www.mobihealthnews.com/20750/glowcaps-now-sold-throuch-cvs-new-randomized-control-trial-launches (Mar. 11, 2013).

"$5 IoT Pill Bottle," https://www.instructables.com/id/5-IoT-Pill-Bottle/ (Apr. 29, 2020).

Hollister, Sean, "Vitality GlowCap Review" (Jan. 13, 2011).

"IoT Pill Bottle," https://www.instructables.com/id/IoT-Pill-Bottle/ (Apr. 29, 2020).

"NantHealth GlowCap 373100," https://fccid.io/2AH33373100 (2020).

Pillsy, Inc. "Never Forget a Pill Again," https://www.pillsy.com/smart-pill-bottle-and-app (2018).

"RX Cap" https://rxcap.com/ (Apr. 29, 2020).

"SMRxT: A Medication Adherence Company," https://www.smrxt.com/ (Apr. 29, 2020).

Wang, Leon "Smart Prescription Bottles," https://medium.com/startupreview/smart-prescription-bottles-e2bd6da30c7d (Aug. 3, 2018).

* cited by examiner

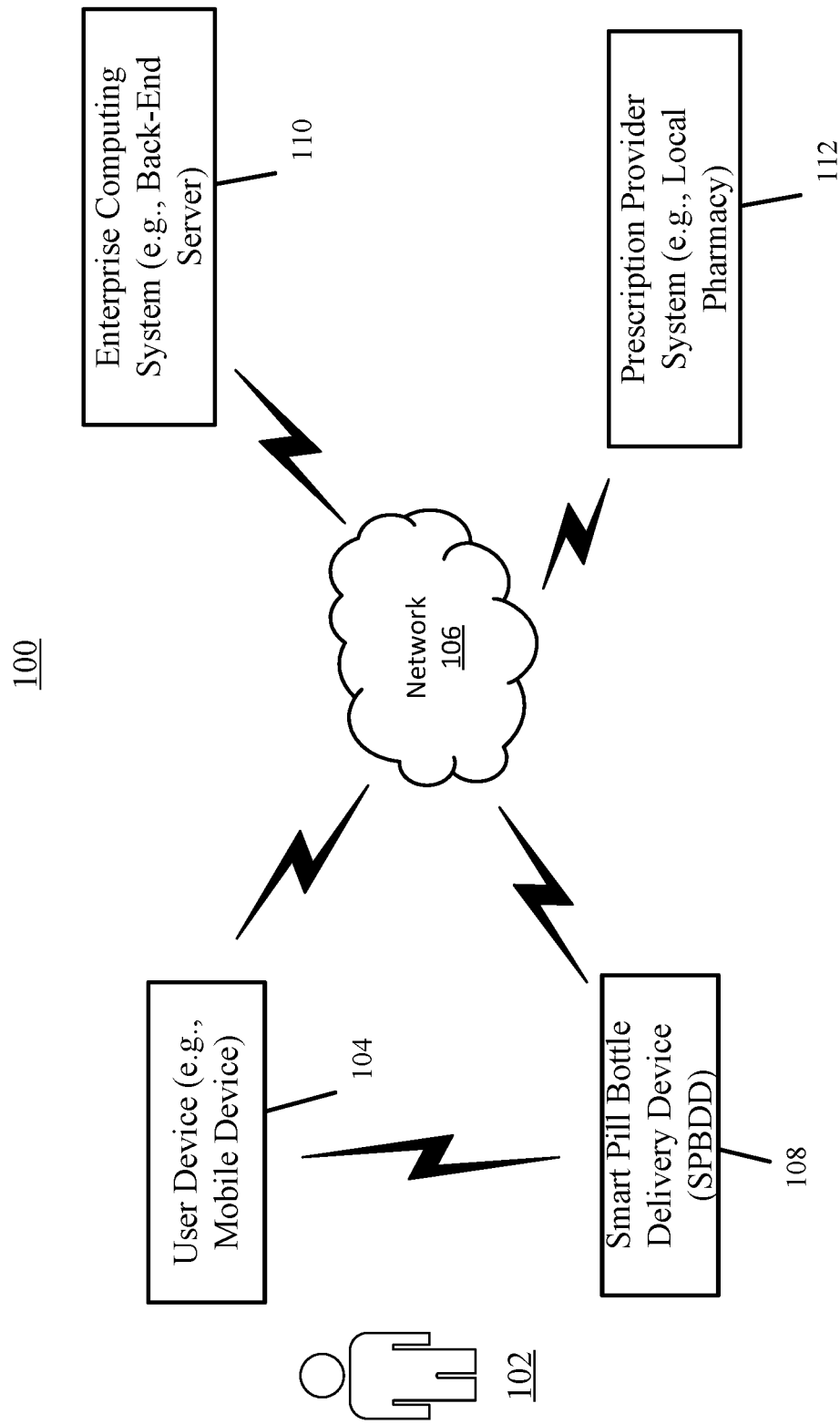

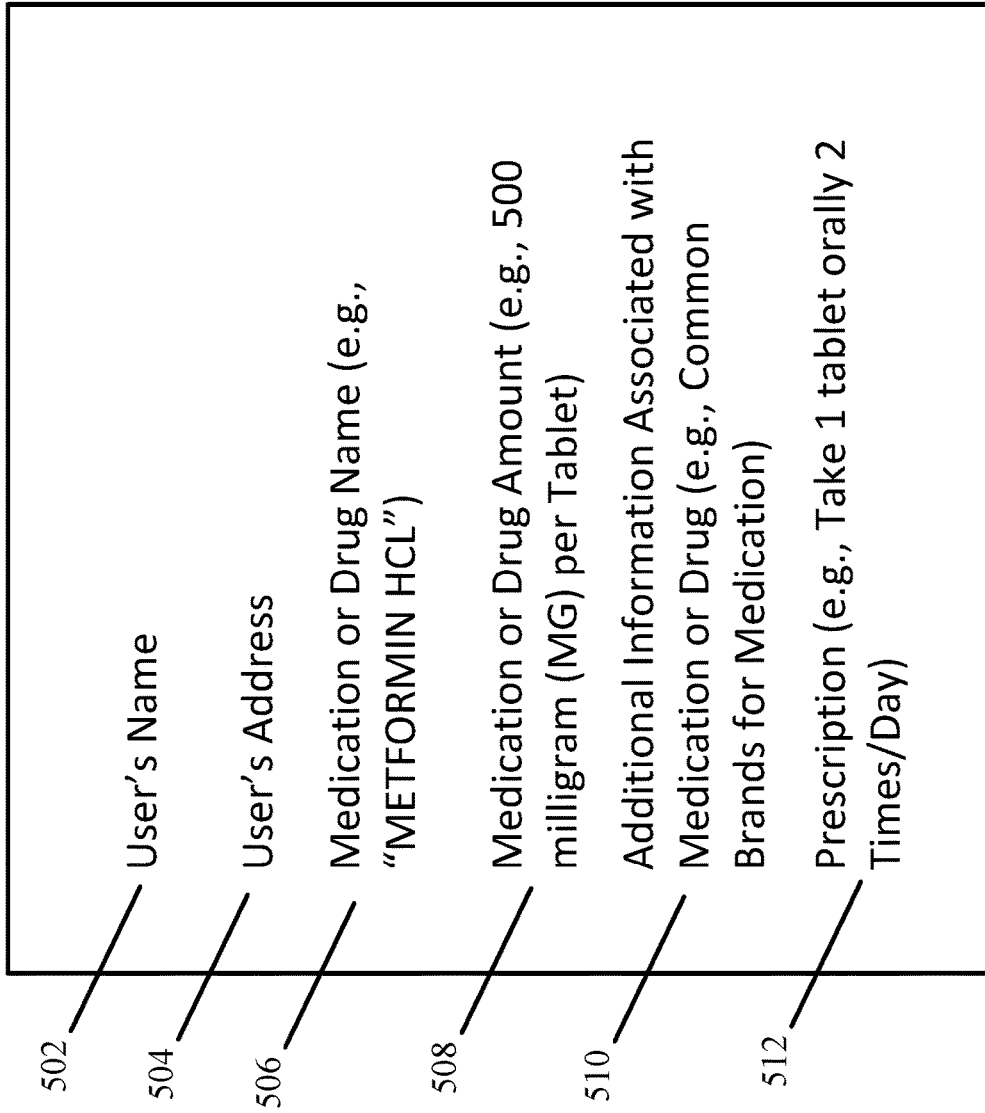

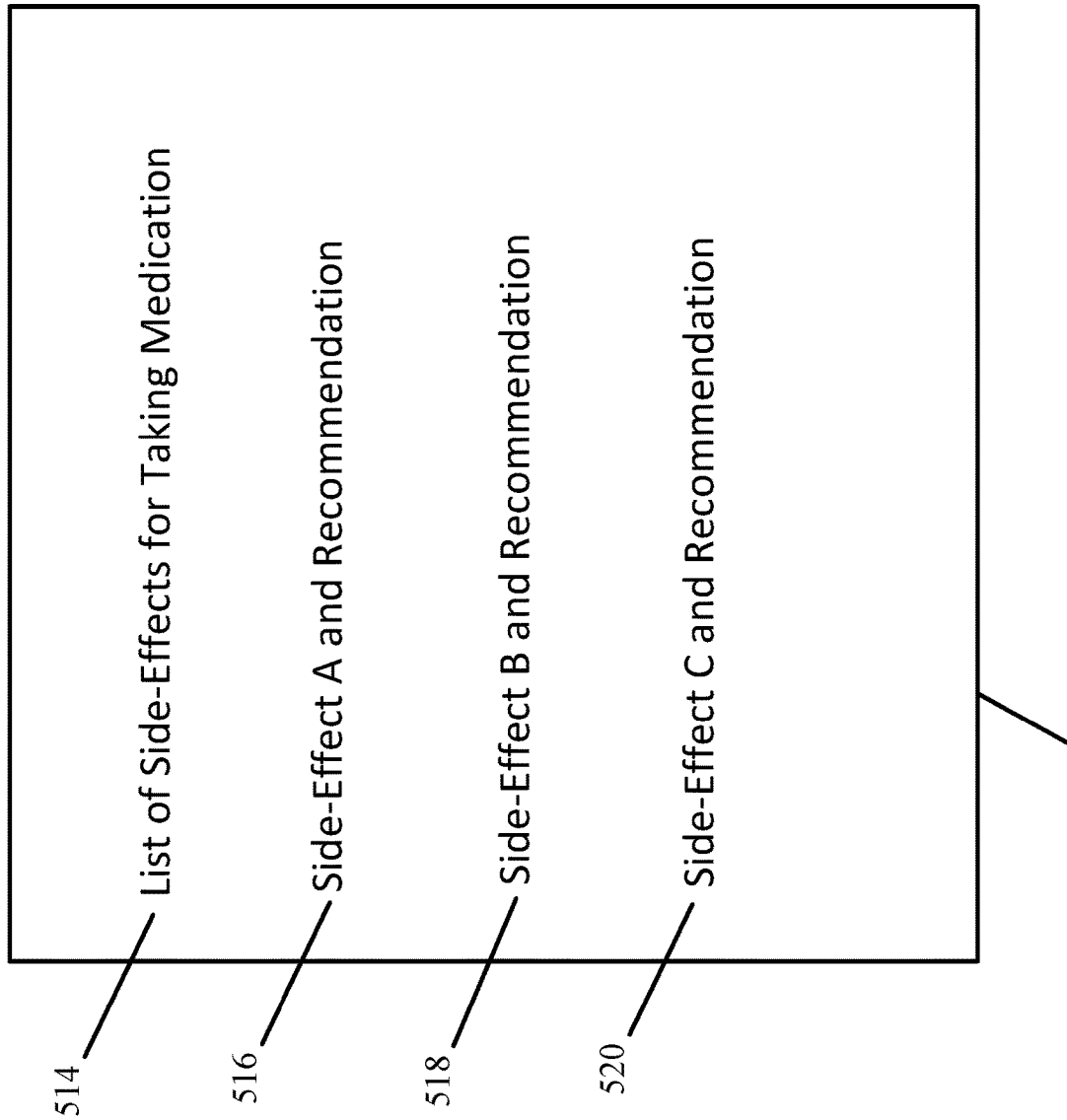

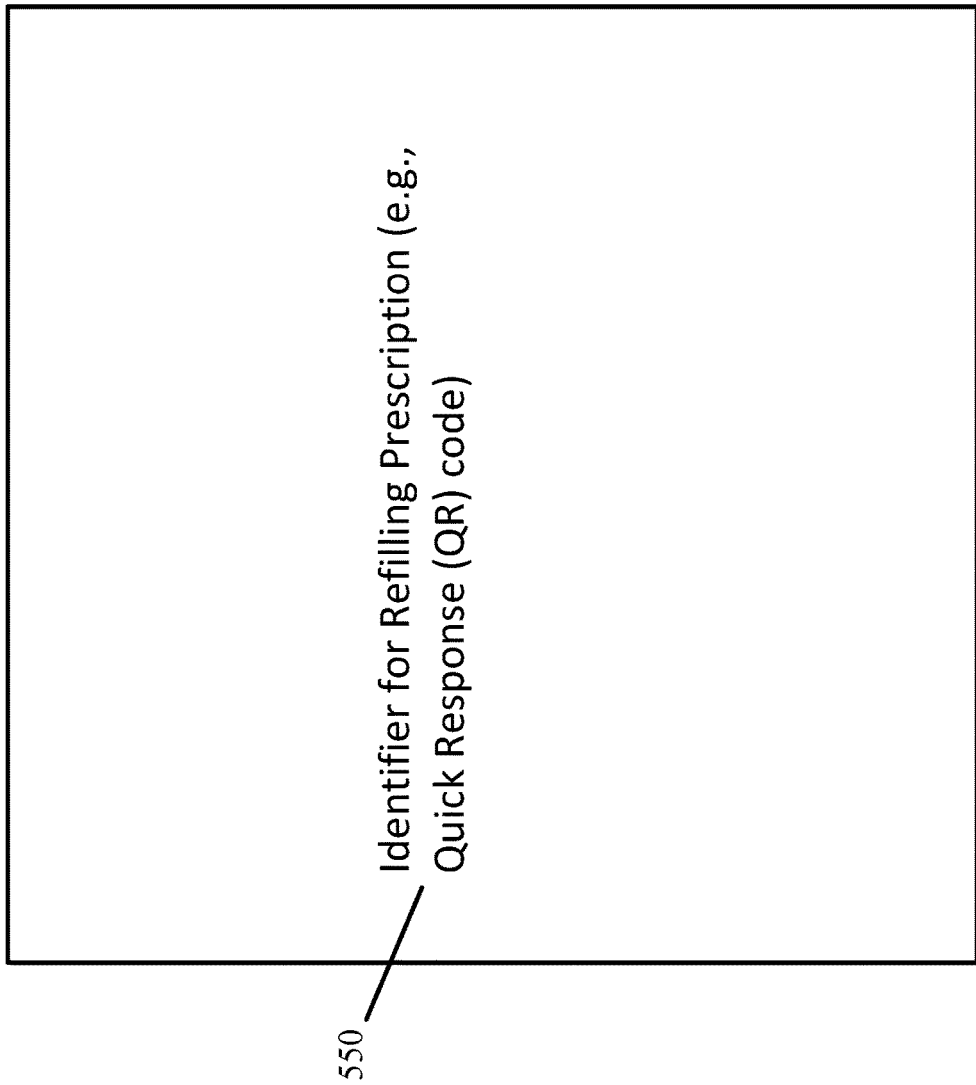

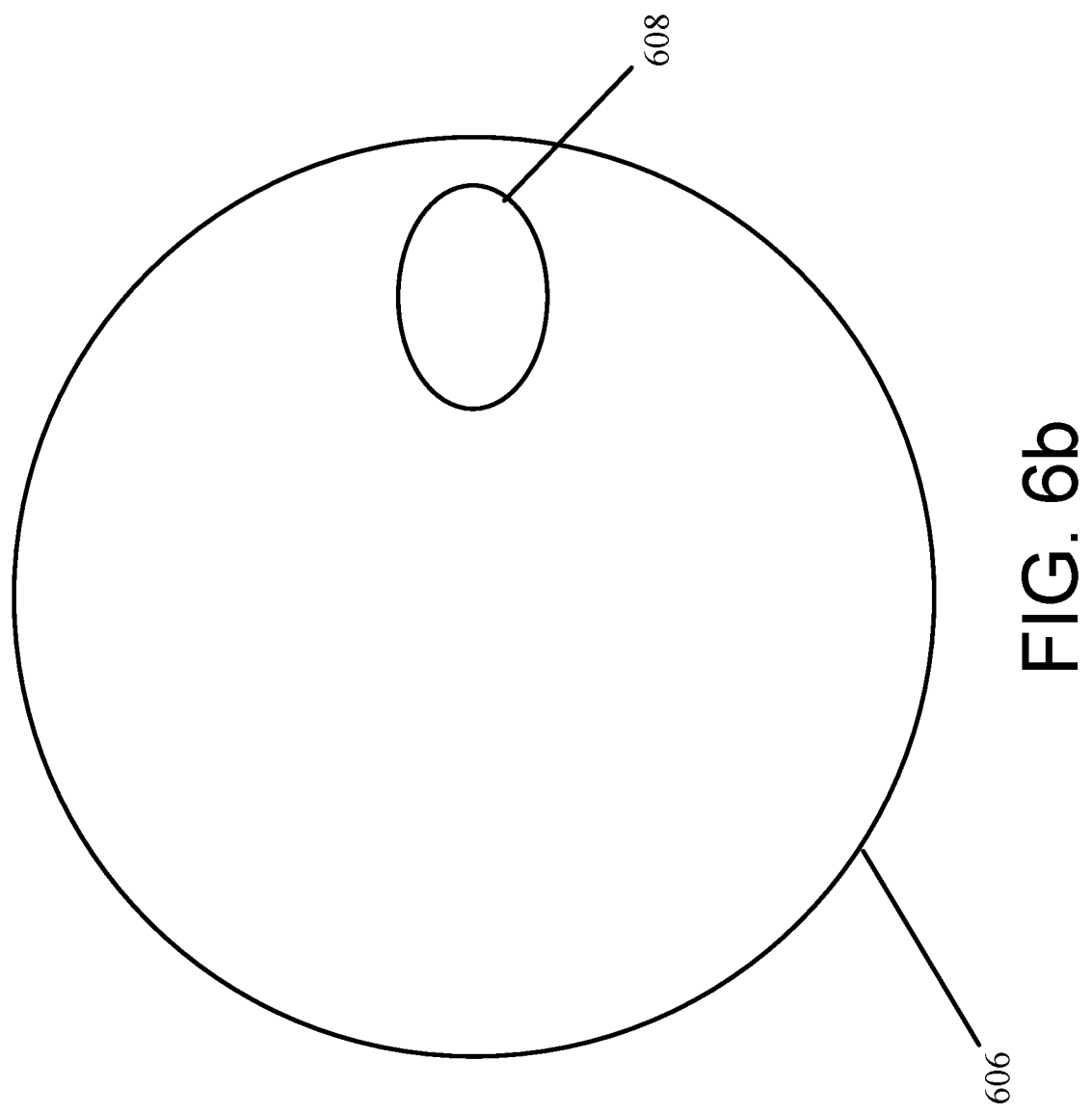

SYSTEMS AND METHODS FOR USING SMART PILL BOTTLES TO DISPLAY PRESCRIPTION INFORMATION TO USERS

BACKGROUND

In some instances, an individual may take multiple different prescription medications. Each of these medications may have different prescriptions (Rx) or instructions associated with the medication. For instance, for a particular medication, the prescription may be to take two tablets a day in the morning and for another medication, the prescription may be to take one tablet every other day with a meal. Therefore, an individual may have difficulty remembering to comply with all of their prescriptions. Additionally, in some situations, the individual may simply forget to take their medication on time. Accordingly, there remains a technical need for using smart pill bottles to display information such as prescriptions to users.

SUMMARY

In some instances, the disclosure provides a method for dispensing medication to a user. The method comprises: based on retrieving a prescription for the user from memory, determining one or more prescription timing intervals indicating times for the user to take one or more medication units of the medication; based on the one or more prescription timing intervals, providing one or more visual notifications indicating for the user to take the one or more medication units, wherein providing the one or more visual notifications comprises displaying a first display screen on a display device; subsequent to providing the one or more visual notifications, detecting, by a smart pill bottle delivery device (SPBDD) and using a position sensor, position information indicating an action performed by the user; and based on the position information indicating the action performed by the user, causing display of a second display screen on the display device, wherein the second display screen displays information that is at least partially different from information displayed on the first display screen.

In some examples, the position information indicating the action performed by the user comprises rotational motion or translational motion of the SPBDD. Furthermore, the SPBDD displays the second display screen on the display device based on the rotational motion or the translational motion of the SPBDD.

In some variations, the position information indicating the action performed by the user comprises one or more non-zero velocity values or one or more non-zero acceleration values of the SPBDD. Furthermore, the SPBDD displays the second display screen on the display device based on the one or more non-zero velocity values or the one or more non-zero acceleration values.

In some instances, the display device is on a user device that is in communication with the SPBDD.

In some examples, the display device is on the SPBDD.

In some variations, the method further comprises: subsequent to displaying the second display screen, receiving, by the SPBDD and using the position sensor, additional position information indicating an additional action performed by the user; and based on the additional position information indicating the additional action performed by the user, displaying, by the SPBDD, a third display screen on the display device of the SPBDD, wherein the third display screen displays information that is at least partially different from information displayed on the first display screen and the second display screen.

In some instances, the SPBDD comprises memory that stores a plurality of sequential display screens. The plurality of sequential display screens includes the first display screen, the second display screen, and at least two additional display screens. The SPBDD displays the second display screen on the display device is further based on the second display screen being a next sequential display screen from the plurality of sequential display screens. The method further comprises: detecting, by the SPBDD and using the position sensor, additional position information indicating one or more additional actions performed by the user; and in response to each additional action of the one or more additional actions, displaying the next sequential display screen from the plurality of sequential display screens on the display device.

In some examples, the SPBDD displays the next sequential display screen from the plurality of sequential display screens on the display device based on a pre-defined time-period.

In some variations, the method further comprises: detecting, by the SPBDD and using a pill cap sensor, pill cap information indicating a dispensing event associated with dispensing the one or more medication units; and in response to detecting the pill cap information indicating the dispensing event, ceasing to display the next sequential display screen from the plurality of sequential display screens in response to each of the additional actions and shutting down the display device.

In some instances, the method further comprises: providing, by the SPBDD, environment information to a user device, wherein the environment information indicates a temperature reading or a humidity reading associated with the SPBDD.

In some examples, the method further comprises: detecting, by the SPBDD and using a pill cap sensor, pill cap information indicating a dispensing event associated with dispensing the one or more medication units; and providing, by the SPBDD, pill bottle information to a second device based on the dispensing event.

In some variations, the second device is a back-end server and the pill bottle information comprises information indicating geographical information associated with a location of where the user took the one or more medication units.

In some instances, the SPBDD comprises a pill dispensing apparatus. The method further comprises: determining, based on the prescription for the user, an amount of the one or more medication units to dispense at each of the one or more prescription timing intervals; and providing instructions to a motor of the pill dispensing apparatus indicating for the motor to dispense the amount of the one or more medication units.

In some examples, the disclosure provides a smart pill bottle comprising: a storage compartment for storing medication for a user and a smart pill bottle delivery device (SPBDD) fastenable to the storage compartment. The SPBDD comprises a position sensor configured to provide position information to one or more processors; a pill cap sensor configured to provide pill cap information to the one or more processors; a display device configured to display information to the user; the one or more processors; and a non-transitory computer-readable medium having processor-executable instructions stored thereon. The processor-executable instructions, when executed, facilitate: based on a prescription for the user, determining one or more prescription timing intervals indicating for the user to take one or more medication units; based on the one or more prescription timing intervals, providing one or more visual notifications indicating for the user to take the one or more medication units, wherein providing the one or more visual notifications comprises displaying a first display screen on the display device; subsequent to providing the one or more visual notifications, receiving, from the position sensor, position information indicating an action performed by the user; and based on the position information indicating the action performed by the user, causing display of a second display screen, wherein the second display screen displays information that is at least partially different from information displayed on the first display screen.

In some variations, the processor-execution instructions, when executed, further facilitate: receiving, from the pill cap sensor, pill cap information indicating a dispensing event associated with dispensing the one or more medication units; and providing, based on the dispensing event, pill bottle information to a user device.

In some instances, the position information indicating the action performed by the user comprises rotational motion or translational motion of the SPBDD. The SPBDD displays the second display screen on the display device based on the rotational motion or the translational motion of the SPBDD.

In some examples, the position information indicating the action performed by the user comprises one or more non-zero velocity values or one or more non-zero acceleration values of the SPBDD. The SPBDD displays the second display screen on the display device based on the one or more non-zero velocity values or the one or more non-zero acceleration values.

In some variations, the SPBDD provides, to a user device, one or more instructions indicating for the user device to display the second display screen.

In some instances, the processor-execution instructions, when executed, further facilitate: subsequent to displaying the second display screen, receiving, by the SPBDD and using the position sensor, additional position information indicating an additional action performed by the user; and based on the additional position information indicating the additional action performed by the user, displaying, by the SPBDD, a third display screen on the display device of the SPBDD, wherein the third display screen displays information that is at least partially different from information displayed on the first display screen and the second display screen.

In some variations, the disclosure provides a non-transitory computer-readable medium having processor-executable instructions stored thereon. The processor-executable instructions, when executed, facilitate: based on retrieving a prescription for a user from memory, determining one or more prescription timing intervals indicating times for the user to take one or more medication units; based on the one or more prescription timing intervals, providing one or more visual notifications indicating for the user to take the one or more medication units, wherein providing the one or more visual notifications comprises displaying a first display screen on a display device; subsequent to providing the one or more visual notifications, detecting, by a smart pill bottle delivery device (SPBDD) and using a position sensor, position information indicating an action performed by the user; and based on the position information indicating the action performed by the user, causing display of a second display screen on the display device, wherein the second display screen displays information that is at least partially different from information displayed on the first display screen.

BRIEF DESCRIPTION OF THE DRAWINGS

The subject technology will be described in even greater detail below based on the exemplary figures, but is not limited to the examples. All features described and/or illustrated herein can be used alone or combined in different combinations. The features and advantages of various examples will become apparent by reading the following detailed description with reference to the attached drawings which illustrate the following:

FIG. 1a is a simplified block diagram depicting an exemplary computing environment in accordance with one or more examples of the present application.

FIG. 2 is a simplified block diagram of one or more devices or systems within the exemplary environment of FIG. 1a.

FIGS. 5a-5g are a plurality of display screens capable of being shown on the display device of the smart pill bottle delivery device in accordance with one or more examples of the present application.

FIGS. 6a and 6b are simplified block diagrams depicting a pill dispensing apparatus in accordance with one or more examples of the present application.

DETAILED DESCRIPTION

Figure 1B:
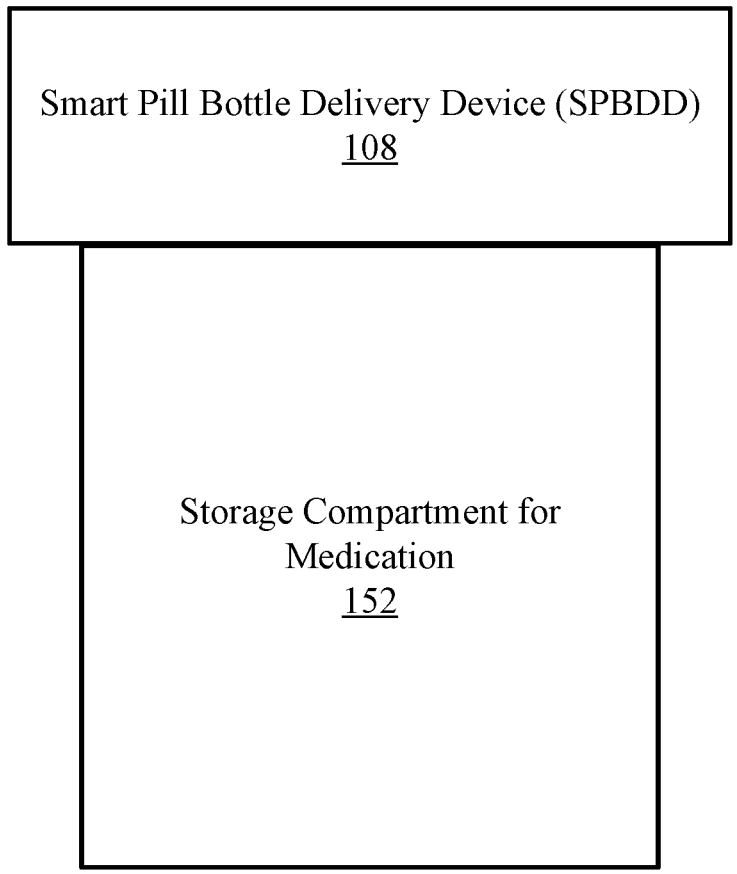
FIG. 1b shows a pill bottle with a smart pill bottle delivery device in accordance with one or more examples of the present application.

Examples of the presented application will now be described more fully hereinafter with reference to the accompanying FIGs., in which some, but not all, examples of the application are shown. Indeed, the application may be exemplified in different forms and should not be construed as limited to the examples set forth herein; rather, these examples are provided so that the application will satisfy applicable legal requirements. Where possible, any terms expressed in the singular form herein are meant to also include the plural form and vice versa, unless explicitly stated otherwise. Also, as used herein, the term "a" and/or "an" shall mean "one or more" even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on".

Systems, methods, and computer program products are herein disclosed that provide for displaying information on a display device of a smart pill bottle delivery device. FIG. 1a is a simplified block diagram depicting an exemplary environment in accordance with an example of the present application. The environment 100 includes an individual (e.g., user) 102, a user device (e.g., mobile device) 104 associated with the user 102, a smart pill bottle delivery device (SPBDD) 108 associated with the user 102, an enterprise computing system (e.g., back-end server) 110, and a prescription provider system (e.g., local pharmacy) 112. Although the entities within environment 100 may be described below and/or depicted in the FIGs. as being singular entities, it will be appreciated that the entities and functionalities discussed herein may be implemented by and/or include one or more entities.

The entities within the environment 100 such as the user device 104, the SPBDD 108, the enterprise computing system 110, and/or the prescription provider system 112 may be in communication with other systems within the environment 100 via the network 106. The network 106 may be a global area network (GAN) such as the Internet, a wide area network (WAN), a local area network (LAN), or any other type of network or combination of networks. The network 106 may provide a wireline, wireless, or a combination of wireline and wireless communication between the entities within the environment 100. Additionally, and/or alternatively, the user device 104 may be in communication with the SPBDD 108 without using the network 106. For instance, the user device 104 may use one or more communication protocols such as WI-FI or BLUETOOTH to communicate with the SPBDD 108.

User 102 may operate, own, and/or otherwise be associated with a user device 104. For instance, the user device 104 may be a mobile phone such as a smartphone that is owned and/or operated by the user 102. The user 102 may provide information to the other entities of environment 100 such as the enterprise computing system 110 and/or the prescription provider system 112 using the user device 104. For example, the user device 104 may receive user input from the user 102 such as indications to download and/or operate a software application associated with an enterprise organization. The enterprise organization may be any type of corporation, company, organization, and/or other institution. The software application may be an application that is used by the user device 104 to communicate with the SPBDD 108. For example, the SPBDD 108 may communicate with and/or provide alerts as well as other information to the user 102 using the software application and the user device 104. Additionally, and/or alternatively, the user device 104 may provide commands, updates, and/or other information such as an updated prescription to the SPBDD 108 using the software application.

The user device 104 may be and/or include, but is not limited to, a desktop, laptop, tablet, mobile device (e.g., smartphone device, or other mobile device), smart watch, an internet of things (IOT) device, or any other type of computing device that generally comprises one or more communication components, one or more processing components, and one or more memory components. The user device 104 may be able to execute software applications managed by, in communication with, and/or otherwise associated with the enterprise organization.

The SPBDD 108 may be any device that provides alerts to the user 102 indicating for the user 102 to take their medication. FIG. 1b shows an exemplary pill bottle 150 (e.g., medication bottle) that includes the SPBDD 108 and a storage compartment for medication 152. The storage compartment 152 may include and/or be any type of container, compartment, and/or storage space that stores medications such as pills, tablets, capsules, and so on. The SPBDD 108 may be a cap or lid for the pill bottle 150 and is fastenable or securable to the storage compartment 152. FIG. 1b is merely an example of the SPBDD 108 and in other examples, the SPBDD 108 may be configured to be used as a lid for a pill packet (e.g., medication packet) and/or other types of pill or medication dispensing containers.

Referring back to FIG. 1a and as will be described in further detail below, the SPBDD 108 may include one or more processors, sensors, memory, and/or output devices such as display devices and/or audio output devices that are used to display notifications to the user 102 to take their medication. For example, the SPBDD 108 may display alerts for the user 102 to take the medication based on a prescription. In other words, a physician may prescribe a prescription (Rx) for a particular medication for the user 102. The SPBDD 108 may receive and/or store the prescription in memory. Based on the prescription, the SPBDD 108 may determine when the user 102 should take the medication and provide alerts, messages, and/or notifications for the user 102 to take medication at a particular time. For example, the prescription may indicate to take one tablet every morning. Based on the prescription, the SPBDD 108 may determine the user 102 should take the medication at 8:00 AM every morning and provide one or more notifications at 8:00 AM every morning for the user 102 to take the medication.

The SPBDD 108 may use output devices such as an audio output device that provides an audio alert for the user 102 to take the medication and a display device that visually displays the alert. For example, at 8:00 AM, the SPBDD 108 may provide an audio alert and a visual alert. The visual alert may include displaying information such as prescription information (e.g., take one tablet every morning) on the display device.

Additionally, and/or alternatively, the SPBDD 108 may include one or more sensors such as a position sensor (e.g., accelerometer, gyroscope, magnetometer, and/or digital compass). The position sensor may provide position information indicating an action performed by the user 102. The action performed by the user 102 may include moving the pill bottle 150 to a different location and/or tapping the pill bottle 150. In other words, when the user 102 physically moves the SPBDD 108 (e.g., pill bottle 150) such as picking up the SPBDD 108, the position sensor may provide information indicating this movement. Based on the position information, the SPBDD 108 may change the display screen shown on the display device from an initial display screen to a different display screen. For instance, the initial display screen may show the prescription from the physician and based on receiving the position information indicating the movement, the SPBDD 108 may show a second display screen indicating side effects of the medication.

In some variations, the SPBDD 108 displays a sequence or series of display screens on the display device. Each of these display screens may show different information and the SPBDD 108 may change to the next display screen based on the received position information from the position sensor. For example, initially, the SPBDD 108 may display a first display screen from the sequence of display screens. Based on position information from the position sensor (e.g., information indicating movement of the SPBDD 108), the SPBDD 108 may cycle through the sequence and display different display screens in a sequential order. After reaching the end of the sequence, the SPBDD 108 may display the first display screen again.

In some instances, the SPBDD 108 may include the storage compartment 152. In other words, the SPBDD 108 may be the entire pill bottle that includes the processor, memory, sensors, and the storage compartment for the medication. The operations, functionalities, and components of the SPBDD 108 will be described in further detail below.

The enterprise computing system 110 is a computing system that is associated with the enterprise organization.

The enterprise computing system 110 includes one or more computing devices, computing platforms, systems, servers, and/or other apparatuses capable of performing tasks, functions, and/or other actions for the enterprise organization. In some instances, the enterprise computing system 110 may, for example, receive and/or provide information from the SPBDD 108, the prescription provider system 112, and/or the user device 104. For instance, the enterprise computing system 110 may receive and/or provide information indicating prescriptions from the SPBDD 108 and/or the user device 104. Additionally, and/or alternatively, the enterprise computing system 110 may determine whether the user 102 is complying with the prescription provided by the physician based on the information from the user device 104 and/or the SPBDD 108.

The enterprise computing system 110 may be implemented using one or more computing platforms, devices, servers, and/or apparatuses. In some variations, the enterprise computing system 110 may be implemented as engines, software functions, and/or applications. In other words, the functionalities of the enterprise computing system 110 and/or the enterprise computing system 110 may be implemented as software instructions stored in storage (e.g., memory) and executed by one or more processors.

The prescription provider system 112 (e.g., a local pharmacy) includes one or more computing devices that are used for receiving prescriptions for a user 102 from a physician and displaying the prescriptions to a technician and/or pharmacist. The prescription provider system 112 may be implemented using one or more computing platforms, devices, servers, and/or otherwise apparatuses that are capable of providing prescription information to the SPBDD 108.

In other words, a physician may prescribe a prescription for the user 102 and use a computing device to provide the information to the prescription provider system 112. A technician and/or pharmacist at the local pharmacy may view the displayed prescription information, verify the prescription is accurate, and fulfill the prescription (e.g., provide and package the medication for the user 102 in a pill bottle and/or packet such as the pill bottle 150). The technician and/or pharmacist may use the one or more computing devices of the prescription provider system 112 to provide the prescription information to the SPBDD 108. The SPBDD 108 may receive the prescription information and store this information in its memory.

It will be appreciated that the exemplary environment depicted in FIG. 1a is merely an example, and that the principles discussed herein may also be applicable to other situations—for example, including other types of institutions, organizations, devices, systems, and network configurations. As will be described herein, the environment 100 may be used by health care enterprise organizations. For example, the enterprise organization may be a health care enterprise organization that provides prescription medications to users including user 102. In some variations, the enterprise organization may operate, manage, manufacture, provide, and/or otherwise be associated with the enterprise computing system 110, the prescription provider system 112, and/or the SPBDD 108.

Figure 2:
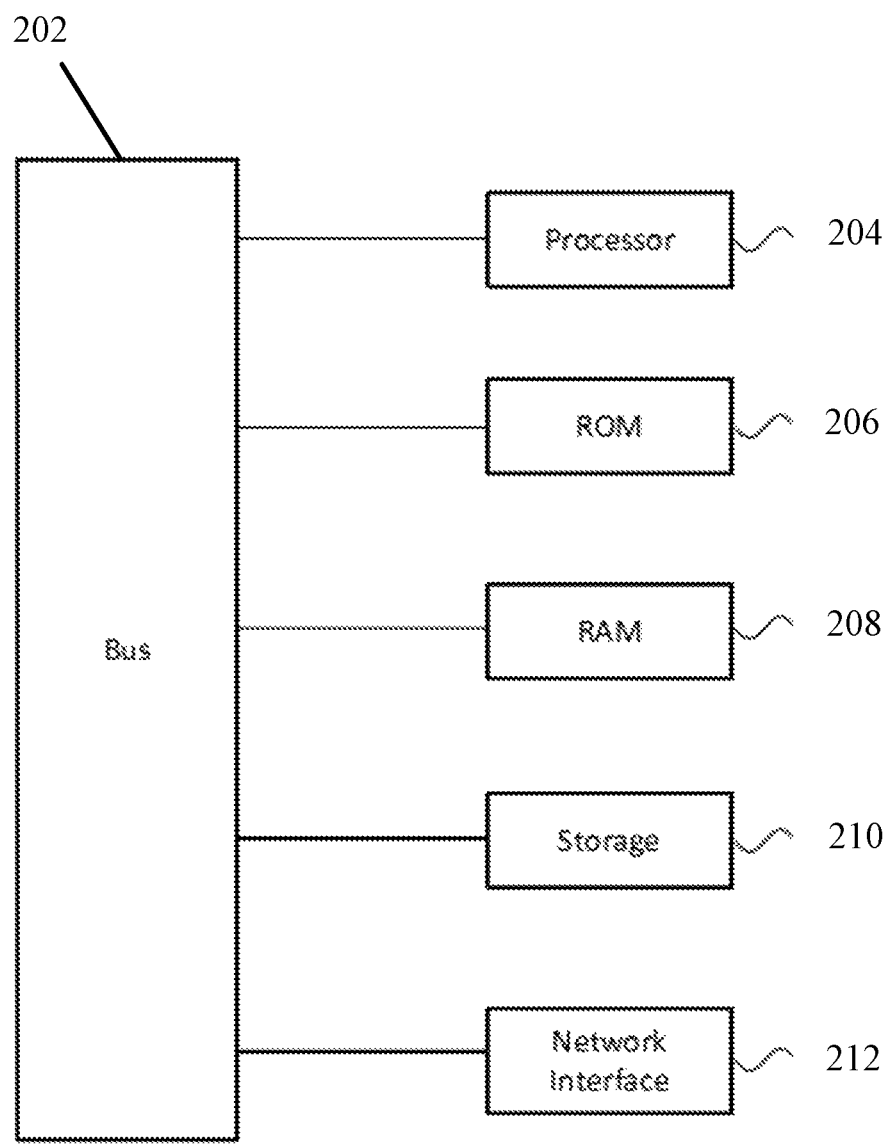

FIG. 2 is a block diagram of an exemplary system and/or device 200 within the environment 100. The device/system 200 includes a processor 204, such as a central processing unit (CPU), controller, and/or logic, that executes computer executable instructions for performing the functions, processes, and/or methods described herein. In some examples, the computer executable instructions are locally stored and accessed from a non-transitory computer readable medium, such as storage 210, which may be a hard drive or flash drive. Read Only Memory (ROM) 206 includes computer executable instructions for initializing the processor 204, while the random-access memory (RAM) 208 is the main memory for loading and processing instructions executed by the processor 204. The network interface 212 may connect to a wired network or cellular network and to a local area network or wide area network, such as the network 106. The device/system 200 may also include a bus 202 that connects the processor 204, ROM 206, RAM 208, storage 210, and/or the network interface 212. The components within the device/system 200 may use the bus 202 to communicate with each other. The components within the device/system 200 are merely exemplary and might not be inclusive of every component, device, computing platform, and/or computing apparatus within the device/system 200. For example, as will be described below, the SPBDD 108 may include some of the components within the device/system 200 and may also include further components such as one or more sensors. Additionally, and/or alternatively, the device/system 200 may further include components that might not be included within every entities of environment 100.

Figure 3:
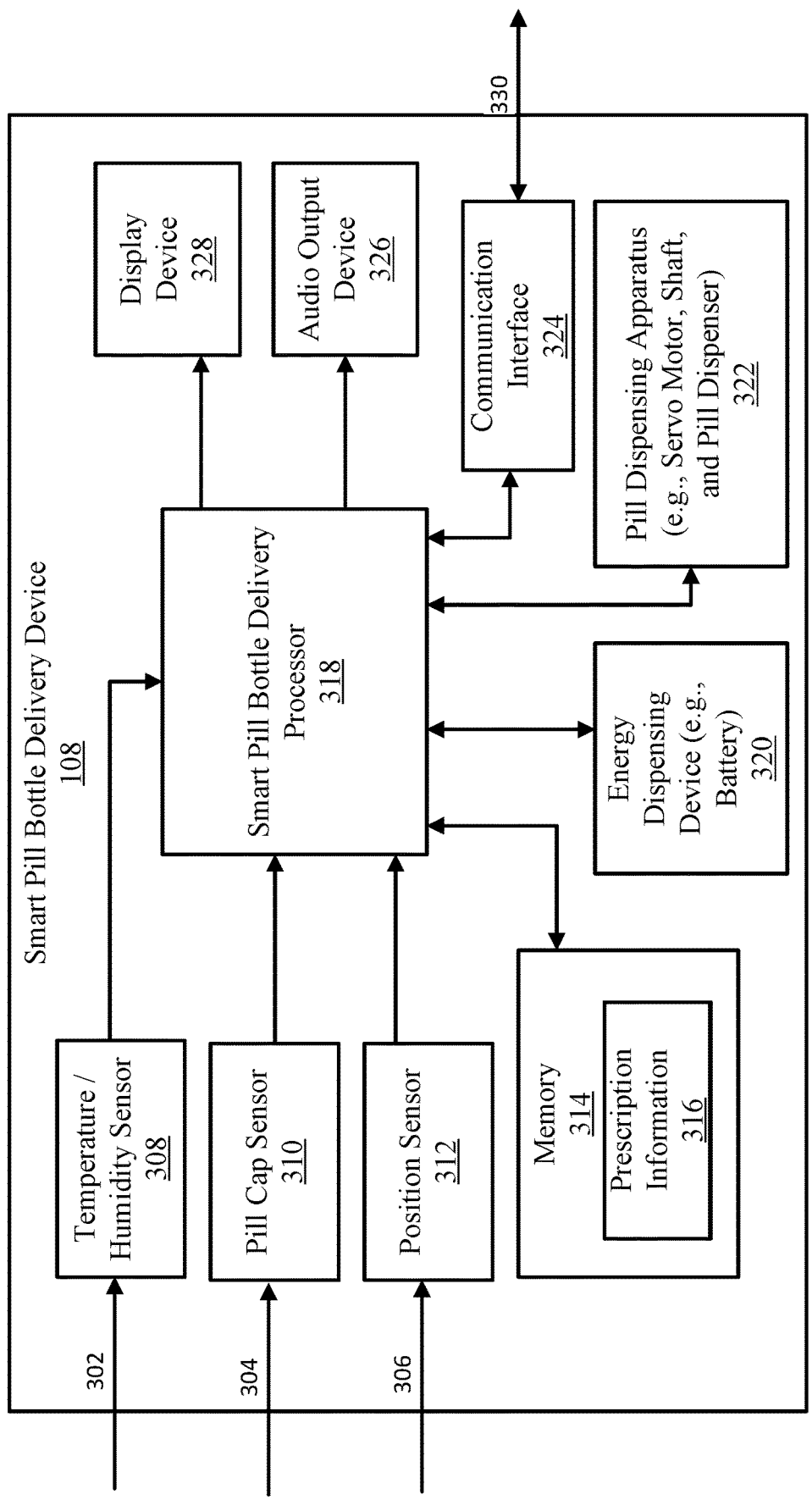
FIG. 3 is another simplified block diagram depicting the smart pill bottle delivery device in accordance with one or more examples of the present application.

FIG. 3 is a simplified block diagram depicting an SPBDD 108 in accordance with one or more examples of the present application. As mentioned above, the SPBDD 108 may be included within a pill bottle (e.g., pill bottle 150), pill packet, and/or other pill dispensing apparatuses. The SPBDD 108 may be operatively coupled to a storage compartment for the medication. Furthermore, the SPBDD 108 may include multiple components such as one or more sensors (e.g., temperature/humidity sensor 308, pill cap sensor 310, and/or position sensor 312), smart pill bottle delivery processors (SPBDP) 318, memory 314, energy dispensing device 320 (e.g., battery), pill dispensing apparatus 322, communication interface 324, and/or output devices (e.g., display device 328 and audio output device 326).

The sensors of the SPBDD 108 include, but are not limited to, temperature/humidity sensors 308, pill cap sensors 310, and position sensors 312. The temperature/humidity sensor 308 receives/detects information 302 indicating one or more temperatures and/or humidity of an area surrounding the SPBDD 108 or pill bottle 150 and/or within the storage compartment 152 where the medication is stored. In other words, the temperature/humidity sensor 308 detects the temperature and/or humidity of the area or environment surrounding the pill bottle and/or within the pill bottle. The temperature/humidity sensor 308 provides the information indicating the temperatures and/or humidity to the SPBDP 318.

In some examples, the temperature/humidity sensor 308 is a single sensor that detects both temperature and humidity. In other examples, the temperature/humidity sensor 308 is two separate entities. In other words, the temperature sensor may be separate from the humidity sensor. The temperature sensor may be any type of sensor that is capable of detecting temperatures and may be/include one or more infrared (IR) temperature sensors, thermistors, thermal cameras, and/or resistance temperature detectors (RTDs). The humidity sensor may detect and measure water vapor including the humidity/moisture of the area surrounding the pill bottle and/or within the pill bottle.

The pill cap sensor 310 receives/detects information 304 indicating a dispensing event (e.g., whether the pill bottle/packet has been opened or closed). The pill cap sensor 310 may be any type of sensor that is capable of detecting whether the pill bottle/packet has been opened or closed and may be/include a reed switch, a proximity switch, and/or a magnetic sensor. For example, when the user 102 opens a pill bottle, the pill cap sensor 310 detects information 304 indicating a disconnect between the SPBDD 108 and the storage compartment 152. For instance, the SPBDD 108 may initially be fastened to the storage compartment 152. The user 102 may unfasten the SPBDD 108 from the storage compartment 152 to take their medication. The pill cap sensor 310 detects the unfastening of the SPBDD 108 from the storage compartment 152 and provides this information to the SPBDP 318.

The position sensor 312 receives/detects positional information 306 indicating an action performed by the user 102. The position sensor 312 may be any type of sensor that is capable of detecting the action and may be/include a digital compass, gyroscope, accelerometer, and/or magnetometer. For example, the position sensor 312 detects information 306 indicating a change in position of the pill bottle/SPBDD 108 (e.g., a change from a first position to a second position) and provides the positional change to the SPBDP 318. In some instances, the change in position may be translational such as movement from one location to another location. In other instances, the change in position may be rotational such as a rotation of certain degrees. In other words, the position sensor 312 may detect the pill bottle 150 has been rotated a certain number of degrees (e.g., 90 degrees). In some examples, the position sensor 312 detects information 306 such as a velocity and/or acceleration of the pill bottle/SPBDD 108. The velocity and/or acceleration may indicate movement of the SPBDD 108 and/or the pill bottle/packet. The position sensor 312 may provide the velocity and/or acceleration to the SPBDP 318.

Additionally, and/or alternatively, the position sensor 312 detects information 306 indicating the user is tapping the pill bottle 150. For instance, the position sensor 312 may continuously detect and provide, to the SPBDP 318, x-axis, y-axis, and/or z-axis coordinates associated with the pill bottle 150 and/or the SPBDD 108. The SPBDP 318 may detect a change of the x-axis, y-axis, and/or z-axis coordinates and based on detecting the change, the SPBDP 318 may determine the user is tapping the SPBDD 108 and/or pill bottle 150. In other words, due to the user tapping the SPBDD 108, the SPBDD 108 may depress slightly causing the SPBDP 318 to detect a change of the x-axis, y-axis, and/or z-axis coordinates. Based on this change, the SPBDP 318 may determine the user is tapping the SPBDD 108. In some examples, the SPBDP 318 may determine the user is tapping the SPBDD 108 and/or pill bottle 150 based on using one of the x, y, or z-axis coordinates. In other examples, the SPBDP 318 may use multiple (e.g., two or three) of the x, y, or z-axis coordinates to determine the user is tapping the SPBDD 108 and/or pill bottle 150. In some instances, the position sensor 312 may be a magnetometer and the SPBDP 318 may use a timing threshold to determine whether there has been a change to the x-axis, y-axis, and/or z-axis coordinates of the pill bottle 150 and/or the SPBDD 108.

While only the temperature/humidity sensors 308, pill cap sensors 310, and position sensors 312 are shown in FIG. 3, in some examples, the SPBDD 108 may include additional sensors. For instance, in some variations, the SPBDD 108 may include a proximity sensor, an image capturing device (e.g., camera), and/or a radio-frequency identification (RFID) sensor. In some instances, the SPBDD 108 may use the proximity sensor to count the number of pills remaining within the pill bottle 150.

The SPBDP 318 may be any type of hardware and/or software logic, such as a central processing unit (CPU), RASPBERRY PI processor/logic, controller, and/or logic, that executes computer executable instructions for performing the functions, processes, and/or methods described herein. For example, the SPBDP 318 retrieves prescription information 316 from memory 314 and based on the prescription information 316 determines when to provide a notification indicating for the user 102 to take their medication. Furthermore, the SPBDP 318 receives sensor information from the one or more sensors (e.g., the temperature/humidity sensors 308, pill cap sensors 310, and position sensors 312). The SPBDP 318 may use the sensor information for one or more functionalities such as changing the display screens shown on the display device 328.

The SPBDD 108 includes memory 314. Memory 314 includes prescription information 316 indicating a prescription for the user 102. For example, the prescription may indicate for the user to take the medication twice a day. The prescription provider system 112 may provide the prescription information to the SPBDD 108. In some examples, during the filling or refilling of the medication, a computing device from the prescription provider system 112 may provide the prescription information to the SPBDD 108. The SPBDD 108 may receive this information using the communication interface 324 and store the information in memory 314.

In some examples, the memory 314 may be and/or include a computer-usable or computer-readable medium such as, but not limited to, an electronic, magnetic, optical, electromagnetic, infrared, or semiconductor computer-readable medium. More specific examples (e.g., a non-exhaustive list) of the computer-readable medium may include the following: an electrical connection having one or more wires; a tangible medium such as a portable computer diskette, a hard disk, a time-dependent access memory (RAM such as the RAM 208), a ROM such as ROM 206, an erasable programmable read-only memory (EPROM or Flash memory), a compact disc read-only memory (CD_ROM), or other tangible optical or magnetic storage device. The computer-readable medium may store computer-readable instructions/program code for carrying out operations of the present application. For example, when executed by the SPBDP 318, the computer-readable instructions/program code may carry out operations described herein.

The SPBDD 108 includes a pill dispensing apparatus 322. The pill dispensing apparatus 322 may include one or more components such as a motor (e.g., servo motor), a pill dispenser, and a shaft operatively coupled to the motor and pill dispenser. The SPBDP 318 may provide instructions for the pill dispensing apparatus 322 to dispense a certain amount of a medication such as a single pill or multiple pills at a particular time. For instance, the prescription information 316 may indicate to take two tablets of medication every four hours. The SPBDP 318 may use a timer or other type of counter and every four hours, may provide instructions or commands to the pill dispensing apparatus 322 to dispense two tablets. The pill dispenser may be any type of apparatus that is capable of being driven by the motor to dispense medications. In some instances, the pill dispenser may encompass the opening of the storage compartment 152 and include one or more openings that are substantially the same size as a pill within the storage compartment 152. The motor may drive the pill dispenser in a rotational motion such that at each rotation, only a known number of tablets (e.g., one tablet) are released from the pill bottle 150. For instance, the instructions may indicate to release two tablets. The pill dispenser may have a singular opening and the motor may drive the pill dispenser approximately 720 degrees (2 revolutions) such that during each revolution, a single tablet is released by the pill dispenser. This will be described in more detail in FIGS. 6a and 6b.

The SPBDD 108 includes a network interface 324. The SPBDP 318 uses the network interface 324 to communicate with other devices and/or systems within the environment 100. The network interface 324 may include the functionalities and/or be the network interface 212 shown in FIG. 2. For example, the SPBDP 318 may receive information 330 from the prescription provider system 112 using the network interface 324. Additionally, the SPBDP 318 may communicate with the user device 104 such as providing alerts and/or information using the network interface 324.

The SPBDD 108 further includes output devices such as an audio output device 326 and display device 328. The output devices may provide a notification such as an alert to the user 102 indicating for the user 102 to take the medication and/or may display the prescription information. For example, the SPBDP 318 may determine, based on the prescription information 316, a timer for dispensing the medication to the user 102. After the timer has concluded, the SPBDP 318 may provide instructions to the output devices to alert the user 102 of taking their medication. For instance, these instructions may indicate for the audio output device 326 to provide an audio alert such as an alarm sound or a text-to-speech indication to the user 102. Additionally, and/or alternatively, these instructions may also indicate for the display device 328 to display a display screen from the memory 314. The display screen may indicate the prescription information 316 (e.g., take two tablets).

The audio output device 326 may be any type of device that outputs audio. For example, the audio output device 326 may be a speaker or speaker system that provides audio output. The audio output device 326 may output distinct sounds such as an alarm sound and/or may incorporate text-to-speech algorithms that output a phrase or sentence indicating for the user 102 to take their medication (e.g., "Please take your medication now"). In some instances, the phrase or sentence may include other phrases or sentences such as ("Ouch, stop that") based on the position sensor 312 indicating movement or tapping of the pill bottle 150.

The display device 328 may be any type of device that is capable of displaying visual information and/or alerts. In some examples, the display device 328 may include a graphical user interface (GUI) and/or may be able to receive input from a user (e.g., touch-screen). As will be described below, the SPBDP 318 may display different display screens on the display device 328 including different information based on received sensor information. In some instances, the display device 328 may further include one or more light emitters such as light emitting diodes (LED) lights. The LED lights may provide an alert indicating for the user 102 to take the medication.

Figure 4:
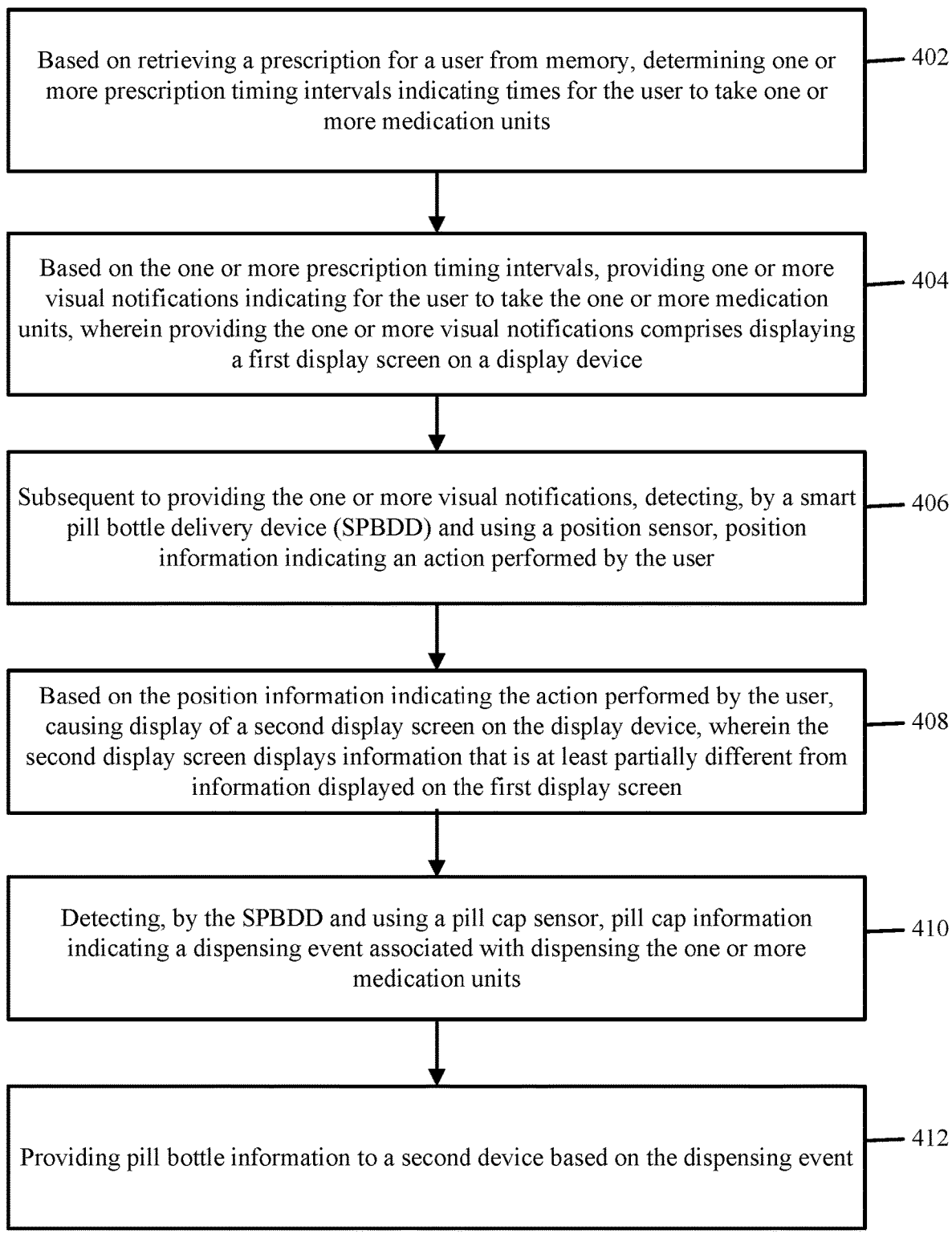
FIG. 4 is an exemplary process for operating the smart pill bottle delivery device in accordance with one or more examples of the present application.

FIG. 4 is an exemplary process 400 for operating the SPBDD 108 to provide information to the user 102 associated with taking their medication in accordance with one or more examples of the present application. The process 400 may be performed by the SPBDD 108 shown in FIG. 3 and in the context of environment 100 of FIG. 1a; however, it will be recognized that an SPBDD 108 that includes additional and/or fewer components as shown in FIG. 3 may be used to perform process 400, that any of the following blocks may be performed in any suitable order, and that the process 400 may be performed in any suitable environment.

The descriptions, illustrations, and processes of FIG. 4 are merely exemplary and the process 400 may use other descriptions, illustrations, and processes for displaying information and/or providing alerts.

At block 402, based on retrieving a prescription for a user 102 from memory 314, the SPBDD 108 determines one or more prescription timing intervals indicating times for the user to take one or more medication units. For example, as described above, the SPBDD 108 may receive prescription information 316 from the prescription provider system 112. The prescription information 316 may be stored in the memory 314 of the SPBDD 108 and may indicate a medical prescription that is prescribed by a physician for the user 102. For instance, the prescription may include instructions for the user 102 to take two pills of a certain medication (e.g., METFORMIN HCL) in the morning.

The SPBDD 108 determines one or more prescription timing intervals based on the prescription information 316. The prescription timing intervals may indicate a time window (e.g., between 8:00 AM to 11:00 AM) or an instance in time (e.g., 11:00 AM) for the user 102 to take the medication. For example, if the prescription indicates to take two pills with breakfast every morning, the SPBDD 108 may determine a time interval that satisfies the prescription (e.g., between 8:00-11:00 AM). In some variations, the prescription may indicate for the user 102 to take medications multiple times during the day. For instance, the prescription may indicate for the user to take the medication three times a day. Based on the prescription, the SPBDD 108 may determine multiple different prescription timing intervals per day (e.g., at 8:00 AM, 12:00 PM, and 6:00 PM).

The one or more medication units may indicate the amount or dose of the medication for the user 102 to take at each of the prescription timing intervals. For instance, each pill, tablet, capsule, and so on may be a single medication unit. In some instances, the medication may be in a liquid form. As such, the medication units may indicate a certain dose (e.g., milliliter (mL)) for the user 102 to take at the prescription timing intervals.

At block 404, based on the one or more prescription timing intervals, the SPBDD 108 provides one or more visual notifications indicating for the user to take the one or more medication units. As mentioned above, the SPBDD 108 includes the display device 328 and may use this display device 328 to display visual notifications or display screens. The visual notifications may include a display screen with text, images, and/or other information associated with the prescription, medication, user 102, and so on. For instance, the SPBDD 108 may display a first display screen on the display device 328 of the SPBDD 108. The first display screen may include text such as "Please Take Your Medication." In other words, at each of the determined prescription timing intervals (e.g., 8:00 AM), the SPBDD 108 may provide visual notifications such as displaying a display screen indicating for the user 102 to take their medication (e.g., "Please Take Your Medication").

The display device 328 may be located on a surface of the SPBDD 108 such that the user 102 may view the visual alert. For instance, in some examples and referring to FIG. 1b, the SPBDD 108 may be part of a pill bottle 150 and in particular, a smart pill cap of the pill bottle 150. The display device 328 may be located on a top surface or portion of the SPBDD 108 that is opposite of the surface or portion is fastenable to the storage compartment 152. Additionally, and/or alternatively, the display device 328 may be located on a side surface of the SPBDD 108.

Additionally, and/or alternatively, the SPBDD 108 may include one or more light emitters (e.g., LED lights). The visual notifications may further include emitting or flashing lights of the SPBDD 108 at a certain frequency.

Additionally, and/or alternatively, the SPBDD 108 may further provide one or more audio notifications for alerting the user 102 to take their medication. For example, based on the prescription timing intervals, the SPBDD 108 may use the audio output device 326 to output distinct sounds and/or phrases or sentences indicating for the user 102 to take their medication (e.g., "Please Take Your Medication").

Additionally, and/or alternatively, the visual notifications including the first display screen may be displayed on a different device such as the user device 104. For example, the user device 104 may include a display device. Based on the one or more prescription timing intervals, the user device 104 may display the one or more visual notifications including the first display screen.

At block 406, subsequent to providing the visual and audio notifications, the SPBDD 108 detects, using the position sensor 312, position information indicating an action performed by the user 102. The action performed by the user 102 may include moving the pill bottle 150 to a different location and/or tapping the pill bottle 150. For instance, the position sensor 312 may detect the action based on detecting rotational motion (e.g., rotating the SPBDD 108 90 degrees) or translational motion (e.g., movement from point A to point B) of the SPBDD 108 and/or the pill bottle 150. Additionally, and/or alternatively, the position information may indicate a non-zero velocity value and/or non-zero acceleration value. Based on the velocity and/or acceleration values, the SPBDD 108 may determine movement of the SPBDD 108 and/or the pill bottle.

At block 408, based on the position information indicating the action performed by the user 102, the SPBDD 108 causes display of a second display screen. The second display screen displays information that is at least partially different from the information (e.g., texts and/or images) displayed on the first display screen. For example, the first display screen may show a message such as "Please Take Your Medication." The second display screen may show different information such as the prescription information 316.

In other words and in some examples, the SPBDD 108 may provide visual and/or audio notifications to the user 102 indicating that it is time for the user 102 to take their medication. This visual notification may be a message such as "Please Take Your Medication". Then, the user 102 may pick up, rotate, tap, and/or move the pill bottle in some manner. The SPBDD 108 may detect this action (e.g., by detecting translational motion, rotational motion, tapping, velocity, and/or acceleration of the SPBDD 108 and/or pill bottle) and change the display screen to show different information such as the prescription (e.g., "Take 1 tablet orally 2 Times/Day"). By changing the display screen based on the motion, the SPBDD 108 may remind the user 102 of the correct prescription prior to the user 102 taking the medication, which may reduce instances where the user 102 takes the wrong amount or dosage of a particular medication.

In some instances, at block 408, based on the position information indicating the action, the SPBDD 108 causes display of the second display screen on the display device 328 of the SPBDD 108. In other words, the SPBDD 108 may display the second display screen (e.g., display the prescription information) on the pill bottle 150. In other instances, at block 408, based on the position information indicating the action, the SPBDD 108 causes display of the second display screen on a different device (e.g., the user device 104) within environment 100. For example, the SPBDD 108 may provide instructions to the user device 104 indicating for the user device 104 to display the second display screen (e.g., display the prescription information). Based on the instructions, the user device 104 may display the second display screen. Additionally, and/or alternatively, if the user device 104 is already displaying the first display screen from block 404, then at block 408, the user device 104 may change from displaying the first display screen to the second display screen.

The first and second display screens described above are merely exemplary and the SPBDD 108 may cause display of additional and/or alternative display screens associated with the medication on the display device 328 of the SPBDD 108 and/or the user device 104. FIGS. 5*a*-5*g* show a plurality of display screens that the SPBDD 108 may use to alert or inform the user 102 of their medication in accordance with blocks 404 and 408. For instance, referring to FIG. 5*a*, the SPBDD 108 may display a display screen on the display device 328 that includes the text "Please Take Your Medication." Referring to FIG. 5*b*, the SPBDD 108 may display a display screen on the display device 328 that includes text indicating the prescription information 316. For example, this display screen may include information such as the user's name 502, the user's address 504, the medication or drug name 506 (e.g., "METFORMIN HCL"), the medication or drug amount 508 (e.g., "500 milligram (MG) per tablet"), additional information associated with the medication or drug 510 (e.g., common brand names for the medication), and the actual prescription 512 (e.g. "Take 1 tablet orally 2 Times/Day"). In some instances, at block 404, the SPBDD 108 may display the display screen from FIG. 5*a* and at block 408, the SPBDD 108 may display the display screen from FIG. 5*b*.

However, in other instances, at blocks 404 and 408, the SPBDD 108 may display other display screens such as the display screens shown in FIGS. 5*c*-5*g*. Referring to FIG. 5*c*, the SPBDD 108 may display a display screen indicating the side effects for taking the medication. For instance, the display screen may indicate a title 514 of the display screen such as "List of Side-Effects for Taking Medication" and then list the side effects 516-520. The side effects 516-520 may further indicate a recommendation if the user 102 experiences the particular side effect. For example, "Side-Effect A and Recommendation" 516 may indicate that if the user 102 experiences vomiting or diarrhea, they should contact their physician.

Figure 5A:
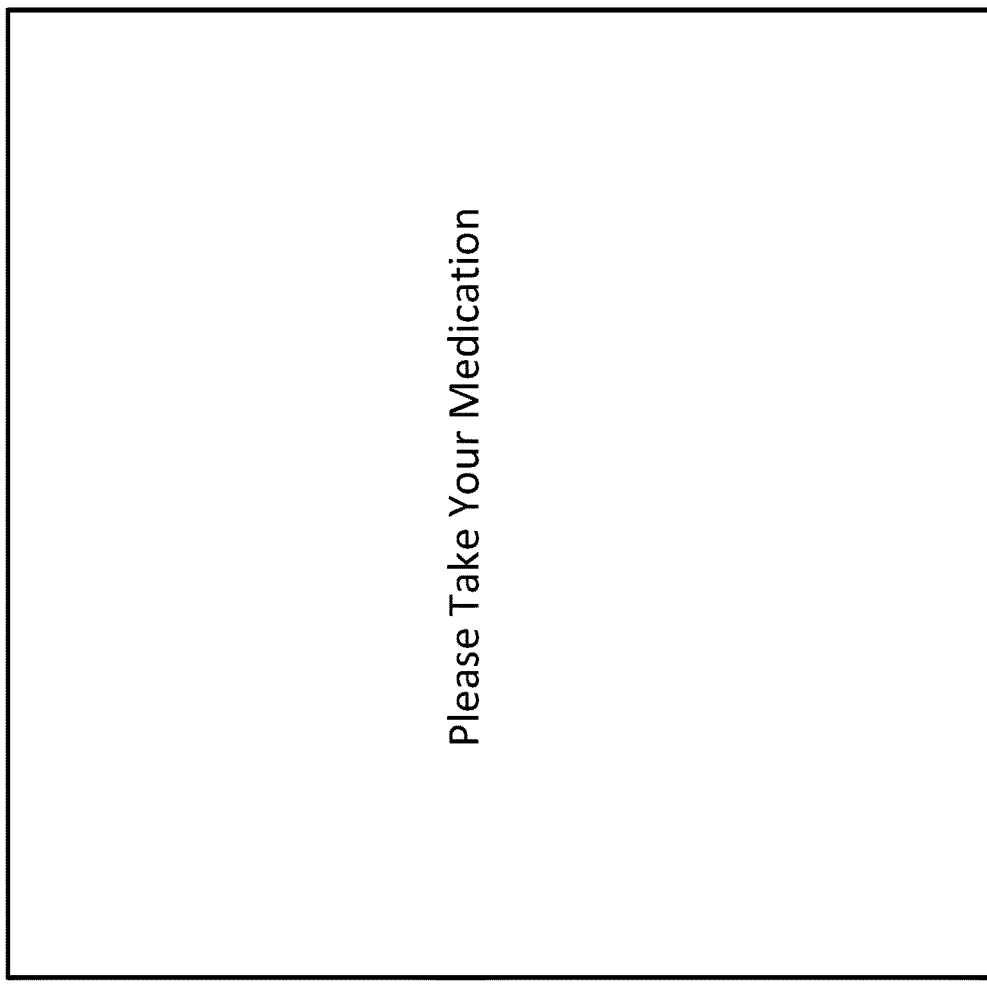
Figure 5D:
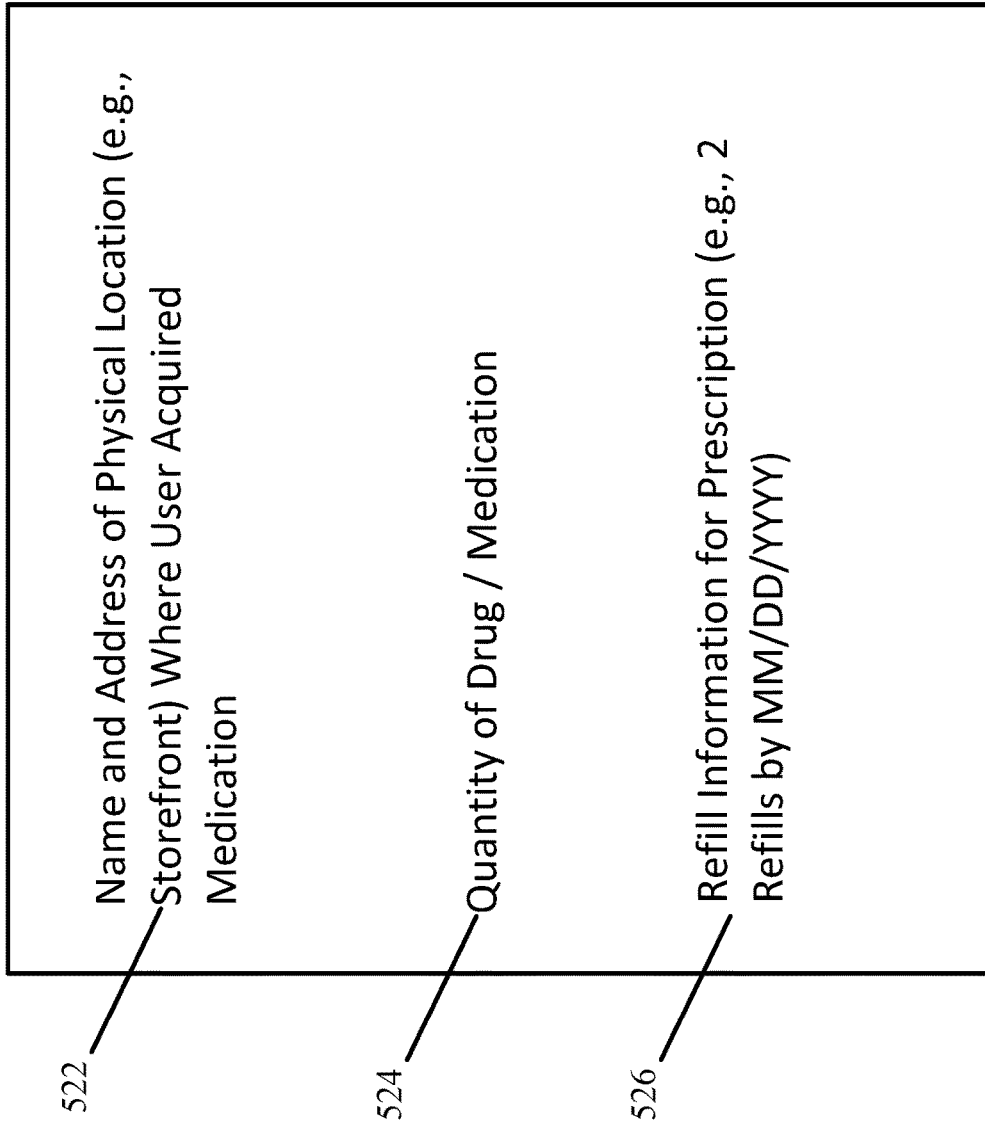

Referring to FIG. 5*d*, the SPBDD 108 may display a display screen indicating a name and address of a physical location where the user 102 acquired the medication 522, a quantity of the drug/medication that has been prescribed 524 (e.g., 60 tablets), and refill information for the prescription 526 (e.g., 2 refills by MM/DD/YYYY). The refill information may indicate the number of refills prescribed by the physician (e.g., 2) and the date when this number of refills expires.

Figure 5E:
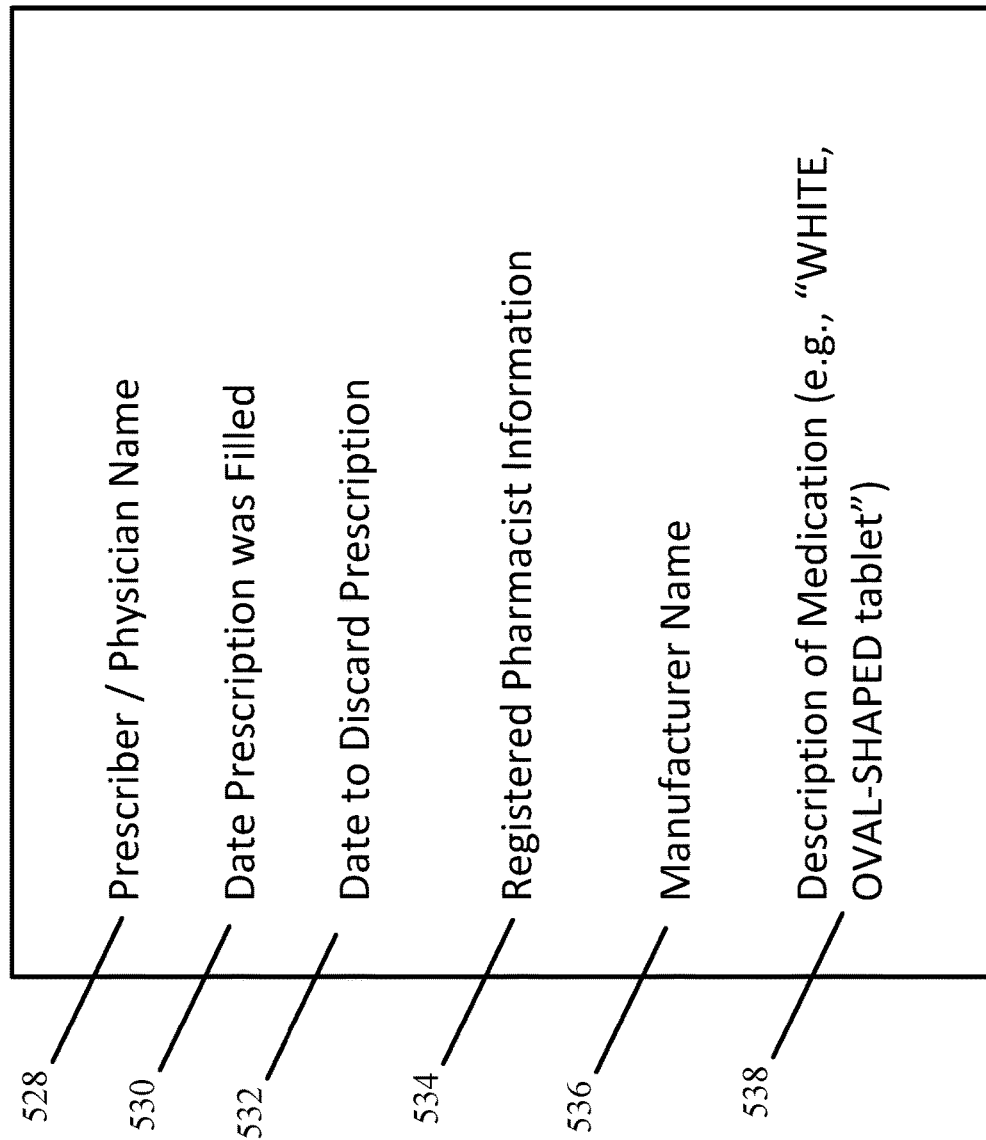

Referring to FIG. 5*e*, the SPBDD 108 may display a display screen indicating a prescriber/physician name 528, a date the prescription was filled 530, a date to discard the prescription 532, the registered pharmacist information 534 that fulfilled the prescription, a manufacturer's name 536 that manufactured the medication, and a description of the medication 538 (e.g., "WHITE, OVAL-SHAPED tablet").

Figure 5F:
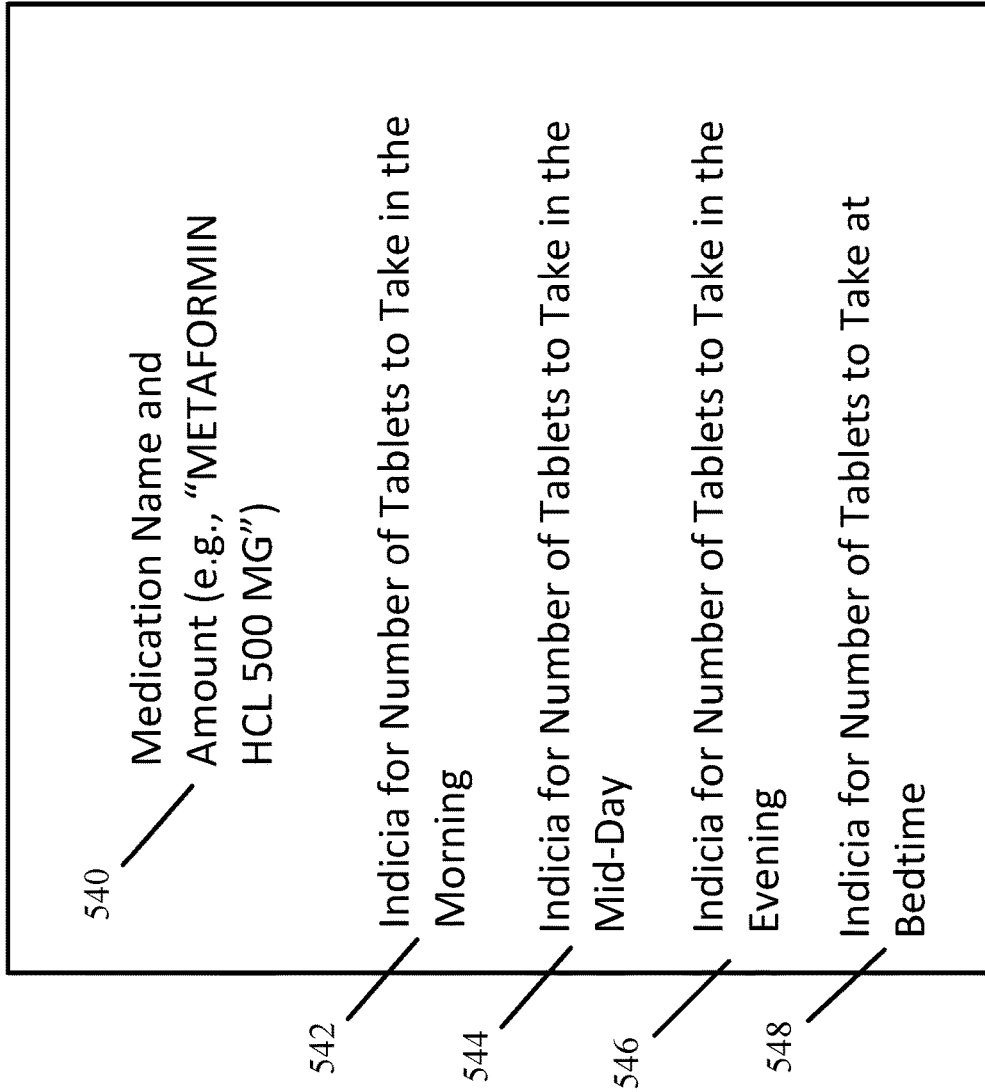

Referring to FIG. 5*f*, the SPBDD 108 may display a display screen indicating a medication name and amount per dose of the medication 540 (e.g., "METAFORMIN HCL 500 MG") and further provide indicia 542-548 indicating a number of tablets to take at different times during the day (e.g., prescription time intervals). The indicia may include a numerical value (e.g., 1 Tablet) and may further include images or text indicating the time of the day such as morning, mid-day, evening, and bedtime. The times during the day may be associated with the prescription timing intervals. For instance and as mentioned above, if the prescription indicates to take 1 tablet during the morning, the prescription time interval may indicate a time window (e.g., 8:00-11:00 AM) or an instance in time (e.g., 10:00 AM). The indicia 542-548 may indicate the determined prescription timing intervals from block 402.

Referring to FIG. 5*g*, the SPBDD 108 may display an identifier for refilling the prescription 550 such as a Quick Response (QR) code. For example, the user 102 may use the user device 104 to scan the displayed QR code shown on the display device 328 of the SPBDD 108. Based on the QR code, the user device 104 may provide, to the enterprise computing system 110 and/or the prescription provider system 112, information indicating to refill the current prescription.

In some examples, the display screens shown on FIGS. 5*a*-5*g* may be stored in memory such as the memory 314. Then, during implementation of process 400 (e.g., at blocks 404 and 408), the SPBDD 108 may retrieve certain display screens from memory 314 and display these display screens on the display device 328. As mentioned above, the display screens described in FIGS. 5*a*-5*g* are merely exemplary and the process 400 may use additional and/or alternative display screens.

In some variations, the user 102 may seek additional information regarding their prescription. For example, at block 408, the SPBDD 108 may display a display screen showing the prescription information such as the display screen shown and described in FIG. 5*b*. The user 102 may seek additional information associated with the prescription information such as the side effects of taking the medication. The SPBDD 108 may transition or change to different display screens based on additional position information from the position sensor 312. The additional position information may indicate another action (e.g., a new or second action) performed by the user 102.

In other words, the user may pick up or rotate the pill bottle 150. The SPBDD 108 may detect this rotational motion and display a display screen showing the prescription information. The user 102 may seek additional information such as the side effects of the medication and may perform another action such as tapping, rotating, and/or moving the pill bottle 150. Based on the position sensor 312 detecting the additional action, the SPBDD 108 may display a new display screen such as the display screen shown in FIG. 5*c* that shows the side effects of the medication.

The first action from block 406 and the second action may be any action that is detectable by the position sensor 312/SPBDD 108 including, but not limited to, tapping the SPBDD 108 or the pill bottle 150, rotating the SPBDD 108 or the pill bottle 150, moving the SPBDD 108 from an initial position to a new position, a non-zero velocity value, and/or a non-zero acceleration value. For instance, the SPBDD 108 may detect the first action as movement from a first position to a second position. Then, based on detecting a second action such as movement from the second position to a new, third position, the SPBDD 108 may change the display screen (e.g., showing side effects instead of the prescription information). Similarly, the SPBDD 108 may detect the first action as a rotation (e.g., 90 degrees), velocity value, or acceleration value. After a brief time period with no motion (e.g., the velocity value/acceleration value returns to 0, the rotation ceases to increase or decrease, or the rotation returns back to substantially the same initial value), the SPBDD 108 may detect a new action such as an additional rotation, a new velocity value, or new acceleration value and change the display screen.

In some variations, the SPBDD 108 may cycle through a plurality of display screens based on detected actions performed by the user 102. For instance, the display screens from FIGS. 5*a*-5*g* may be a sequence of display screens and the SPBDD 108 may cycle through and display these display screens sequentially based on the detected actions. In other words, initially, at block 404, the SPBDD 108 may display a first display screen such as the one shown in FIG. 5*a*. Then, based on receiving position information indicating an action at block 406, the SPBDD 108 may display a second display screen such as the one shown in FIG. 5*b*. The SPBDD 108 may receive new actions and after receiving each new action, the SPBDD 108 may cycle through and display the next display screens from the sequence (e.g., after the first new action, the display screen from FIG. 5*c* is shown; after the second new action, the display screen form FIG. 5*d* is shown, and so on). If the SPBDD 108 receives a new action and is displaying the last display screen from the sequence (e.g., display screen shown in FIG. 5*g*), then the SPBDD 108 may return back to the beginning of the sequence and display the initial display screen again (e.g., display screen shown in FIG. 5*a*).

In some instances, the SPBDD 108 may cycle through a plurality of display screens based on a pre-determined or pre-defined time-period. For instance, the display screens from FIGS. 5*a*-5*g* may be a sequence of display screens and the SPBDD 108 may cycle through and display these display screens sequentially after a time-period (e.g., 15 seconds). For example, the SPBDD 108 may first display a first display screen such as the one shown in FIG. 5*a*. Then, based on receiving position information indicating an action at block 406, the SPBDD 108 may display a second display screen such as the one shown in FIG. 5*b*. After a certain amount of time has elapsed (e.g., 15 seconds), the SPBDD 108 may display the next display screen within the sequence such as the third display screen (e.g., the display screen shown in FIG. 5*c*). This may continue and each time the pre-determined/pre-defined time-period concludes, the SPBDD 108 may display the next display screen within the sequence. In some variations, the SPBDD 108 may cycle through the plurality of display screens based on the time-period and the detected actions. For instance, if the SPBDD 108 receives a detected action, then it may display a next display screen in the sequence. Otherwise, if the SPBDD 108 does not receive an additional action within a certain time-period, then it may display the next display screen from the sequence based on the time-period concluding.

At block 410, the SPBDD 108 receives, from a pill cap sensor 310, pill cap information 304 indicating a dispensing event associated with dispensing the one or more medication units. The dispensing event may be a disconnection event such as opening or unfastening of the pill bottle so that the user 102 may be able to take the medication. For instance, as described above, the pill cap sensor 310 may be a reed switch and/or a magnetic sensor that detects a disconnect between the SPBDD 108 and the storage compartment 152. The SPBDD 108 may receive information indicating the disconnect (e.g., dispensing event).

In some examples, in response to receiving the dispensing event, the SPBDD 108 may cease cycling through the plurality of display screens based on the detected additional actions and/or the pre-determined/pre-defined time-period. In other words, after receiving the disconnection event (e.g., the user 102 is able to or has taken the medication), the SPBDD 108 may override displaying the next display screen in the sequence and display a final display screen such as the display screen of FIG. 5*b* showing the prescription information 316 or might turn off the display device 328 to conserve battery power for the battery 320.

At block 412, the SPBDD 108 provides pill bottle information to a second device (e.g., the user device 104, the prescription provider system 112, and/or the enterprise computing system 110) based on the dispensing event. The pill bottle information may indicate information such as the user 102 has taken their medication, the pill bottle has encountered a dispensing event (e.g., unfastening of the pill bottle), a geographical location indicating an approximate location of where the user 102 took their medication, changes to the orientation of the pill bottle 150, and/or additional information. In other words, after the user 102 opens the pill bottle 150 to take their medication, the SPBDD 108 detects the opening and provides information to a second device such as the user device 104.

In some instances, the SPBDD 108 may provide alerts or notifications to the user device 104 and cause the user device 104 to display the alerts. For instance, the temperature and humidity sensor 308 may receive/detect temperature/humidity information 302. The SPBDD 108 may provide the temperature/humidity information 302 to the user device 104. For instance, the SPBDD 108 may determine whether the detected temperature or humidity of the area surrounding the SPBDD 108 or within the storage compartment 152 is within a certain range (e.g., above and/or below a threshold). If the temperature or humidity is determined to not be within the certain range (e.g., above the threshold or below the threshold), the SPBDD 108 may provide an alert or notification to the user device 104 indicating that the temperature and/or humidity is not within the certain range and for the user 102 to move the pill bottle 150.

In some examples, the SPBDD 108 may provide pill bottle information to a second device such as the user device 104 if the pill cap sensor 310 detects a dispensing event. For instance, the SPBDD 108 may communicate with the user device 104 using any type of wireless communication protocol such as BLUETOOTH, WI-FI, and so on. The SPBDD 108 may provide the pill bottle information such as changes to the temperature/humidity, when to take the medication, if the medicine should be taken now, and/or changes to the orientation of the pill bottle 150. The user device 104 may record/store the pill bottle information.

In some examples, referring to block 404, the SPBDD 108 may use/set a timer or a counter based on the prescription timing intervals. Based on the timer or counter concluding, the SPBDD 108 may provide the one or more visual notifications indicating for the user to take the one or more medication units. For example, the prescription timing intervals indicate for the user 102 to take the prescription in the morning at 10:00 AM. The SPBDD 108 may set a timer or counter that concludes at 10:00 AM. Based on the timer or counter concluding at 10:00 AM, the SPBDD 108 may provide the one or more visual notifications. Then, in blocks 410 and 412, after receiving the pill cap information indicating a dispensing event (e.g., opening of the pill bottle 150), the SPBDD 108 may reset the counter or timer based on the next prescription timing interval. For instance, if the prescription indicates to take a tablet every morning. Then, the SPBDD 108 may reset the counter or timer to conclude in another 24 hours. In other instances, if the prescription indicates to take the medication three times a day, then the SPBDD 108 may determine the prescription timing intervals to be 8:00 AM, 12:00 PM, and 5:00 PM. In such instances, the SPBDD 108 may reset the timer for the next prescription interval.

In some variations, the prescription may indicate for the user 102 to take the medication in the morning and evening and the SPBDD 108 may determine the prescription timing intervals for these as time ranges (e.g., for morning as 8:00 AM to 11:00 AM and for the evening as 6:00 PM to 9:00 PM). In such instances, the SPBDD 108 may set the timer or counter to elapse at any time within the time ranges such as at the beginning of the time range (e.g., 8:00 AM for the morning), in the middle of the time range (e.g., 9:30 AM), or at the end of the time range (e.g., 11:00 AM). After taking the medication (e.g., the dispensing event), the SPBDD 108 may reset the counter or timer for the next prescription timing interval (e.g., for the evening time interval).

In some instances, the user device 104 may also include a timer or counter indicating for the user 102 to take the medication. For instance, if the prescription indicates for the user to take the medication at 8:00 AM and in addition to the SPBDD 108 setting a counter/timer, the user device 104 may also set a counter/timer. Based on the counter/timer concluding on the user device 104, the user device 104 may display an alert or notification to remind the user 102 to take their medication. In some variations and referring to block 402, after determining the one or more prescription timing intervals (e.g., 8:00 AM), the SPBDD 108 may provide the prescription timing intervals to the user device 104. The user device 104 may set the counter/timer based on the prescription timing intervals. In some examples and referring to block 412, the SPBDD 108 may provide pill bottle information to the user device 104 based on the dispensing event (e.g., opening of the pill bottle). Based on receiving the pill bottle information, the user device 104 may reset the counter/timer for the next prescription timing interval.

In some instances and referring to block 412, the SPBDD 108 may provide pill bottle information to enterprise computing system 110. The pill bottle information may indicate when the user 102 took the medication such as a time/date stamp (e.g., an instance in time that the dispensing event detected by the pill cap sensor 310 occurred), the number of pills left within the pill bottle 150 (e.g., the prescription information may indicate the number of pills in the original subscription and based on the number of dispensing events the SPBDD 108 may determine/calculate the number of pills left within the bottle 150), temperature/humidity information, when the user 102 should take the medicine (e.g., prescription timing intervals), geographical information indicating where the user 102 took the medication, and/or changes to the orientation of the pill bottle 150. In some variations, the SPBDD 108 may provide the pill bottle information to the user device 104 and the user device 104 may forward this information to the enterprise computing system 110.

In some examples, after receiving the pill bottle information, the enterprise computing system 110 may display the received information such as when the user 102 took the medication over a time period and the number of pills left within the bottle. Additionally, and/or alternatively, the enterprise computing system 110 may forward the information to the prescription provider system 112 (e.g., local pharmacy). In some variations, the enterprise computing system 110 may use the pill bottle information for analytics such as determining whether the user 102 is taking their medication or why the user 102 is not taking their medication. For example, the enterprise computing system 110 may input the pill bottle information into one or more machine learning algorithms/datasets to determine this information. The pill bottle information may include a time stamp (e.g., a time/date stamp) indicating when the user 102 is taking their medication and/or the number of pills the user 102 took at that time. Based on the time stamp, the enterprise computing system 110 may determine whether the user is following the prescription provided by their physician.

In some examples, based on the pill bottle information, the enterprise computing system 110 may determine/detect an abnormality or problem associated with the medication and/or the user taking the medication. For example, the enterprise computing system 110 receive information indicating an event associated with the user 102. For instance, the event may be a side-effect and/or reported feedback from the user 102 to the physician. The enterprise computing system 110 may compare the event with the pill bottle information (e.g., the time stamp) to determine abnormalities or problems (e.g., potential side-effects) associated with the medication and/or with the user 102 taking the medication.

In some variations, the enterprise computing system 110 and/or the prescription provider system 112 may provide updates to the user's 102 prescription information. For instance, the enterprise computing system 110 and/or the prescription provider system 112 may provide an update for the prescription information and forward this update to the SPBDD 108. The SPBDD 108 may update the prescription information 316 in the memory 314 accordingly. Then, referring to process 400, the SPBDD 108 may display the updated prescription information and/or update the prescription timing intervals. In other words, a pharmacist, technician, and/or physician may update a prescription for the user 102 and push the information to the SPBDD 108 via network 106. For instance, the user 102 may complain to the physician about a side effect due to the user 102 being sensitive to the medication. Accordingly, the physician may forward information to the enterprise computing system 110 and/or the prescription provider system 112 to update the prescription. The enterprise computing system 110 and/or the prescription provider system 112 may provide the update the prescription information in the SPBDD 108 based on the update.

In some examples, the pill dispensing apparatus 322 may dispense a set number of pills based on the prescription information 316. For example, the prescription information 316 may indicate to take two tablets in the morning. Based on the prescription information 316, the SPBDD 108 may provide instructions to the pill dispensing apparatus 322 to dispense two tablets at the indicated time. Based on the instructions, the pill dispensing apparatus 322 may dispense the two tablets.

Figure 6A:
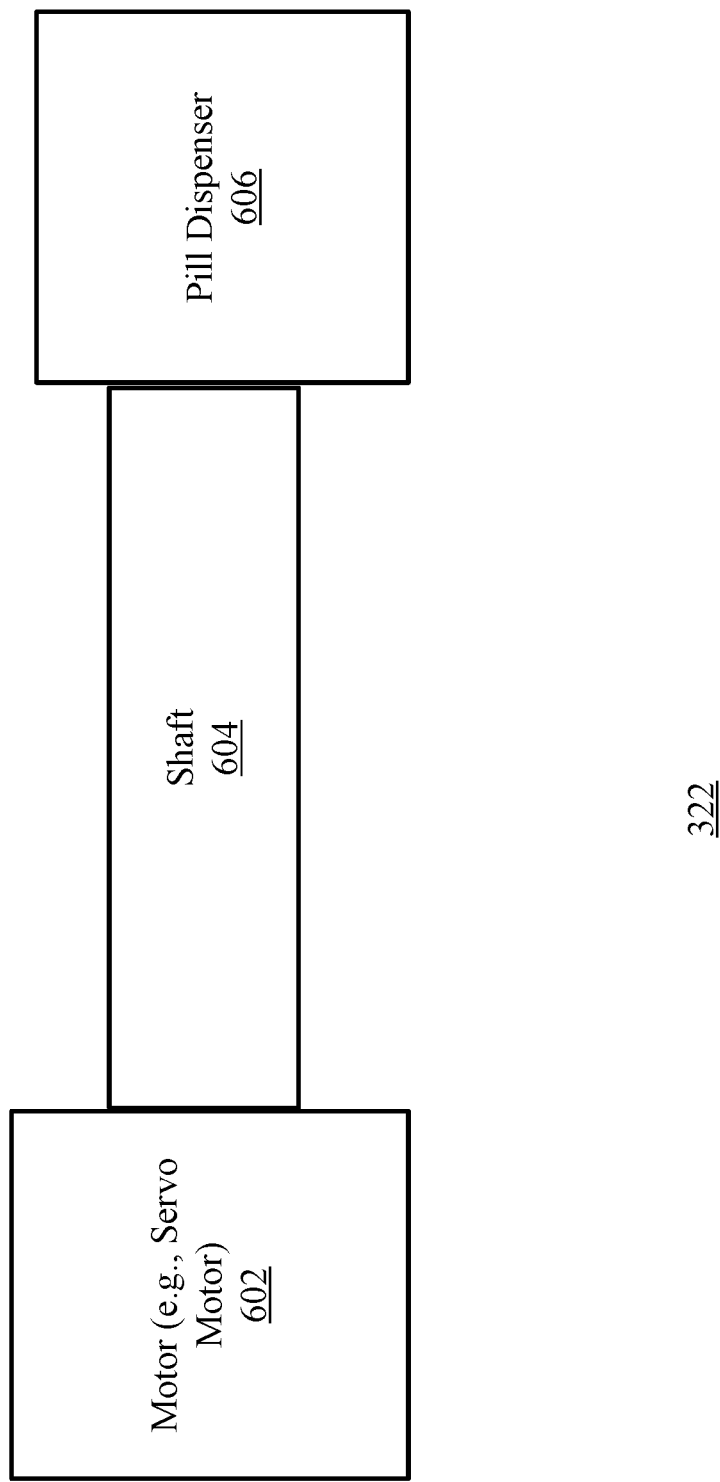

FIGS. 6a and 6b show an exemplary pill dispensing apparatus 322. Referring to FIG. 6a, the pill dispensing apparatus 322 includes a motor 602 such as a servo motor, a shaft 604 that is operatively coupled to the motor 602 and the pill dispenser 606, and a pill dispenser 606 that dispenses pills. FIG. 6b shows an exemplary pill dispenser 606. For instance, the pill dispenser 606 may be circular in shape such that it encompasses or envelops an opening of the storage container 152. The pill dispenser 606 may include an opening 608 that may be an approximate size of a tablet. Based on the instructions, the motor 602 may drive the pill dispenser 606 to rotate a certain number of degrees and/or revolutions. For instance, if the prescription indicates to dispense two tablets, the motor 602 may drive the pill dispenser 606 to rotate two revolutions such that two tablets are dispensed to the user 102.

In some variations, the SPBDD 108 may communicate (e.g., provide information/alerts) with another device (e.g., user device 104) within the environment 100. For instance, without any user interaction, the SPBDD 108 may provide information to the user device 104 indicating the pill bottle 150 is low on pills and/or empty. Additionally, and/or alternatively, the SPBDD 108 may provide instructions automatically to the user device 104 and/or the prescription provider system 112 (e.g., local pharmacy) to refill the prescription. For instance, based on determining the pill bottle 150 is low on pills and/or empty (e.g., based on using a proximity sensor and/or the pill dispensing apparatus 322), the SPBDD 108 may provide instructions indicating for the local pharmacy to refill the medication based on the prescription information.

In some examples, the SPBDD 108 may include a display screen that initiates and/or permits interactions or communications with another device within environment 100. For example, the software application executing on the user device 104 may include a message system that allows a user and/or another operator of the user device 104 to provide messages, alerts, and/or other types of information to the SPBDD 108. The SPBDD 108 may display a display screen showing the messages, alerts, and/or other types of information from the user device 104. Additionally, and/or alternatively, the SPBDD 108 may initiate and/or permit interactions or communications with certain individuals such as a pharmacist, technician, and/or physician. For instance, the SPBDD 108 may include an input device that permits the user to provide information such as messages (e.g., audio messages and/or text messages) or alerts to the pharmacist, technician, and/or physician. The SPBDD 108 may receive information or alerts from the pharmacist, technician, and/or physician and display a display screen indicating the communication from these individuals.

In some instances, the SPBDD 108 may include a push/panic button. Based on actuation of the push/panic button, the SPBDD 108 may provide an alert (e.g., the medication within the pill bottle 150 is running low and/or empty) to the user device 104 and/or another device within the environment 100. In some instances, the display device 328 may be a user interface that receives inputs from the user 102. In other words, the display device 328 may be a touch-screen and may display a push/panic button on the touch screen. Based on the user input, the SPBDD 108 may provide an alert to the user device 104 and/or another device within the environment 100.

It will be appreciated that the figures of the present application and their corresponding descriptions are merely exemplary, and that the application is not limited to these exemplary situations.

It will further be appreciated by those of skill in the art that the execution of the various machine-implemented processes and steps described herein may occur via the computerized execution of processor-executable instructions stored on a non-transitory computer-readable medium, e.g., random access memory (RAM), read-only memory (ROM), programmable read-only memory (PROM), volatile, nonvolatile, or other electronic memory mechanism. Thus, for example, the operations described herein as being performed by computing devices and/or components thereof may be carried out by according to processor-executable instructions and/or installed applications corresponding to software, firmware, and/or computer hardware.

The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the application and does not pose a limitation on the scope of the application unless otherwise claimed. No language in the specification should be construed as indicating any non-claimed element as essential to the practice of the application.

It will be appreciated that the examples of the application described herein are merely exemplary. Variations of these examples may become apparent to those of ordinary skill in the art upon reading the foregoing description. The inventor expects skilled artisans to employ such variations as appropriate, and the inventor intends for the application to be practiced otherwise than as specifically described herein. Accordingly, this application includes all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

The invention claimed is:

1. A method for dispensing medication to a user, comprising:
    based on retrieving a prescription for the user from memory, determining one or more prescription timing intervals indicating times for the user to take one or more medication units of the medication;
    based on the one or more prescription timing intervals, providing one or more visual notifications indicating for the user to take the one or more medication units, wherein providing the one or more visual notifications comprises displaying a first display screen on a display device, wherein the display device is on a smart pill bottle delivery device (SPBDD);
    subsequent to providing the one or more visual notifications, detecting, by the SPBDD and using a position sensor, position information indicating an action performed by the user;
    based on the position information indicating the action performed by the user, causing display of a second display screen on the display device, wherein the second display screen displays information that is different from information displayed on the first display screen;
    subsequent to displaying the second display screen, receiving, by the SPBDD and using the position sensor, additional position information indicating an additional action performed by the user; and
    based on the additional position information indicating the additional action performed by the user, displaying, by the SPBDD, a third display screen on the display device of the SPBDD, wherein the third display screen displays information that is different from information displayed on the first display screen and the second display screen.

2. The method of claim 1, wherein the position information indicating the action performed by the user comprises rotational motion or translational motion of the SPBDD, and wherein displaying the second display screen on the display device is based on the rotational motion or the translational motion of the SPBDD.

3. The method of claim 1, wherein the position information indicating the action performed by the user comprises one or more non-zero velocity values or one or more non-zero acceleration values of the SPBDD, and wherein displaying the second display screen on the display device is based on the one or more non-zero velocity values or the one or more non-zero acceleration values.

4. The method of claim 1, wherein the SPBDD comprises memory that stores a plurality of sequential display screens, wherein the plurality of sequential display screens includes the first display screen, the second display screen, and the third display screen,
    wherein displaying the second display screen on the display device based on the positional information indicating the action performed by the user is further based on the second display screen being a next sequential display screen from the plurality of sequential display screens.

5. The method of claim 4, wherein displaying the next sequential display screen from the plurality of sequential display screens on the display device is further based on a pre-defined time-period.

6. The method of claim 4, wherein the method further comprises:
    detecting, by the SPBDD and using a pill cap sensor, pill cap information indicating a dispensing event associated with dispensing the one or more medication units; and
    in response to detecting the pill cap information indicating the dispensing event, shutting down the display device.

7. The method of claim 1, wherein the method further comprises:
    providing, by the SPBDD, environment information to a user device, wherein the environment information indicates a temperature reading or a humidity reading associated with the SPBDD.

8. The method of claim 1, wherein the method further comprises:
    detecting, by the SPBDD and using a pill cap sensor, pill cap information indicating a dispensing event associated with dispensing the one or more medication units; and
    providing, by the SPBDD, pill bottle information to a second device based on the dispensing event.

9. The method of claim 8, wherein the second device is a back-end server, and wherein the pill bottle information comprises information indicating geographical information associated with a location of where the user took the one or more medication units.

10. The method of claim 8, wherein the SPBDD comprises a pill dispensing apparatus, and wherein the method further comprises:

determining, based on the prescription for the user, an amount of the one or more medication units to dispense at each of the one or more prescription timing intervals; and providing instructions to a motor of the pill dispensing apparatus indicating for the motor to dispense the amount of the one or more medication units.

11. A smart pill bottle, comprising:
a storage compartment for storing medication for a user; and
a smart pill bottle delivery device (SPBDD) fastenable to the storage compartment, comprising:
  a position sensor configured to provide position information to one or more processors;
  a pill cap sensor configured to provide pill cap information to the one or more processors;
  a display device configured to display information to the user;
  the one or more processors; and
  a non-transitory computer-readable medium having processor-executable instructions stored thereon, wherein the processor-executable instructions, when executed, facilitate:
    based on a prescription for the user, determining one or more prescription timing intervals indicating for the user to take one or more medication units;
    based on the one or more prescription timing intervals, providing one or more visual notifications indicating for the user to take the one or more medication units, wherein providing the one or more visual notifications comprises displaying a first display screen on the display device;
    subsequent to providing the one or more visual notifications, receiving, from the position sensor, position information indicating an action performed by the user;
    based on the position information indicating the action performed by the user, causing display of a second display screen, wherein the second display screen displays information that is different from information displayed on the first display screen;
    subsequent to displaying the second display screen, receiving, using the position sensor, additional position information indicating an additional action performed by the user; and
    based on the additional position information indicating the additional action performed by the user, displaying a third display screen on the display device of the SPBDD, wherein the third display screen displays information that is different from information displayed on the first display screen and the second display screen.

12. The smart pill bottle of claim 11, wherein the processor-execution instructions, when executed, further facilitate:
receiving, from the pill cap sensor, pill cap information indicating a dispensing event associated with dispensing the one or more medication units; and
providing, based on the dispensing event, pill bottle information to a user device.

13. The smart pill bottle of claim 11, wherein the position information indicating the action performed by the user comprises rotational motion or translational motion of the SPBDD, and wherein displaying the second display screen on the display device is based on the rotational motion or the translational motion of the SPBDD.

14. The smart pill bottle of claim 11, wherein the position information indicating the action performed by the user comprises one or more non-zero velocity values or one or more non-zero acceleration values of the SPBDD, and wherein displaying the second display screen on the display device is based on the one or more non-zero velocity values or the one or more non-zero acceleration values.

15. A non-transitory computer-readable medium having processor-executable instructions stored thereon, wherein the processor-executable instructions, when executed, facilitate:
based on retrieving a prescription for a user from memory, determining one or more prescription timing intervals indicating times for the user to take one or more medication units;
based on the one or more prescription timing intervals, providing one or more visual notifications indicating for the user to take the one or more medication units, wherein providing the one or more visual notifications comprises displaying a first display screen on a display device, wherein the display device is on a smart pill bottle delivery device (SPBDD);
subsequent to providing the one or more visual notifications, detecting, by the SPBDD and using a position sensor, position information indicating an action performed by the user;
based on the position information indicating the action performed by the user, causing display of a second display screen on the display device, wherein the second display screen displays information that is different from information displayed on the first display screen;
subsequent to displaying the second display screen, receiving, using the position sensor, additional position information indicating an additional action performed by the user; and
based on the additional position information indicating the additional action performed by the user, displaying a third display screen on the display device of the SPBDD, wherein the third display screen displays information that is different from information displayed on the first display screen and the second display screen.

16. The smart pill bottle of claim 11, wherein the processor-execution instructions, when executed, further facilitate:
providing environment information to a user device, wherein the environment information indicates a temperature reading or a humidity reading associated with the SPBDD.

17. The smart pill bottle of claim 11, wherein the processor-execution instructions, when executed, further facilitate:
detecting, using a pill cap sensor, pill cap information indicating a dispensing event associated with dispensing the one or more medication units; and
providing pill bottle information to a second device based on the dispensing event.

18. The smart pill bottle of claim 17, wherein the second device is a back-end server, and wherein the pill bottle information comprises information indicating geographical information associated with a location of where the user took the one or more medication units.

19. The non-transitory computer-readable medium of claim 15, wherein the position information indicating the action performed by the user comprises rotational motion or translational motion of the SPBDD, and wherein displaying the second display screen on the display device is based on the rotational motion or the translational motion of the SPBDD.

20. The non-transitory computer-readable medium of claim 15, wherein the position information indicating the action performed by the user comprises one or more non-zero velocity values or one or more non-zero acceleration values of the SPBDD, and wherein displaying the second display screen on the display device is based on the one or more non-zero velocity values or the one or more non-zero acceleration values.

* * * * *